(12) United States Patent
Rohrman et al.

(10) Patent No.: US 11,421,262 B2
(45) Date of Patent: Aug. 23, 2022

(54) SERIAL FORMATION OF TERNARY COMPLEX SPECIES

(71) Applicant: Omniome, Inc., San Diego, CA (US)

(72) Inventors: Brittany A. Rohrman, La Jolla, CA (US); Denis Malyshev, La Jolla, CA (US); Morassa Mohseni Middleton, San Diego, CA (US); Arnold Oliphant, Morgan Hill, CA (US)

(73) Assignee: PACIFIC BIOSCIENCES OF CALIFORNIA, INC., Menlo Park, CA (US)

(*) Notice: Subject to any disclaimer, the term of this patent is extended or adjusted under 35 U.S.C. 154(b) by 204 days.

(21) Appl. No.: 16/518,321

(22) Filed: Jul. 22, 2019

(65) Prior Publication Data

US 2020/0032317 A1    Jan. 30, 2020

Related U.S. Application Data

(60) Provisional application No. 62/702,468, filed on Jul. 24, 2018.

(51) Int. Cl.
| | | |
|---|---|---|
| *C12Q 1/6806* | (2018.01) | |
| *C12Q 1/686* | (2018.01) | |
| *C12Q 1/6816* | (2018.01) | |

(52) U.S. Cl.
CPC .......... *C12Q 1/6806* (2013.01); *C12Q 1/686* (2013.01); *C12Q 1/6816* (2013.01)

(58) Field of Classification Search
CPC ............ C12Q 2565/518; C12Q 1/6869; C12Q 2535/122
See application file for complete search history.

(56) References Cited

U.S. PATENT DOCUMENTS

| | | |
|---|---|---|
| 7,057,026 B2 | 6/2006 | Barnes et al. |
| 7,414,116 B2 | 8/2008 | Milton et al. |
| 7,427,673 B2 | 9/2008 | Balasubramanian et al. |
| 7,482,120 B2 | 1/2009 | Buzby |
| 7,544,794 B1 | 6/2009 | Benner et al. |
| 7,871,771 B2 | 1/2011 | Fuller et al. |
| 7,906,284 B2 | 3/2011 | Turner et al. |
| 7,956,171 B2 | 6/2011 | Siddiqi et al. |
| 7,960,116 B2 | 6/2011 | Eid et al. |
| 8,034,923 B1 | 10/2011 | Benner et al. |
| 8,071,755 B2 | 12/2011 | Efcavitch et al. |
| 8,399,196 B2 | 3/2013 | Hoser |
| 8,632,975 B2 | 1/2014 | Vander Horn et al. |
| 8,652,781 B2 | 2/2014 | Korlach et al. |
| 8,808,989 B1 | 8/2014 | Siddiqi et al. |
| 9,279,154 B2 | 6/2016 | Previte et al. |
| 9,399,798 B2 | 7/2016 | Morris et al. |
| 9,951,385 B1 | 4/2018 | Vijayan et al. |
| 10,077,470 B2 | 9/2018 | Vijayan et al. |
| 10,161,003 B2 | 12/2018 | Stromberg et al. |
| 10,246,744 B2 | 4/2019 | Vijayan et al. |
| 10,253,352 B2 | 4/2019 | Nguyen et al. |
| 2010/0330570 A1* | 12/2010 | Vander Horn ........... C12Q 1/68 435/6.11 |
| 2017/0314064 A1 | 11/2017 | Iyidogan et al. |
| 2017/0314072 A1 | 11/2017 | Vijayan et al. |
| 2018/0044715 A1 | 2/2018 | Iyidogan et al. |
| 2018/0044727 A1 | 2/2018 | Vijayan et al. |
| 2018/0155698 A1 | 6/2018 | Iyidogan et al. |
| 2018/0187245 A1 | 7/2018 | Dambacher et al. |
| 2018/0208983 A1 | 7/2018 | Dambacher et al. |
| 2019/0048404 A1 | 2/2019 | Dambacher |
| 2019/0119740 A1 | 4/2019 | Ahn et al. |

FOREIGN PATENT DOCUMENTS

| | | |
|---|---|---|
| WO | 9106678 A1 | 5/1991 |
| WO | 2004018497 A2 | 3/2004 |
| WO | 2007123744 A2 | 11/2007 |
| WO | 2017014762 A1 | 1/2017 |
| WO | 2017184996 A1 | 10/2017 |

OTHER PUBLICATIONS

Mitra, R.D. et al., Fluorescent in situ sequencing on polymerase colonies, Anal. Biochem., vol. 320, pp. 55-65 (Year: 2003).*
Seo, T.S. et al., Photocleavable fluorescent nucleotides for DNA sequencing on a chip constructed by site-specific coupling chemistry, PNAS, vol. 101, pp. 5488-5493 (Year: 2004).*
PCT/US2019/042789, "International Preliminary Report on Patentability", dated Feb. 4, 2021, 8 pages.
PCT/US2019/042789, "International Search Report and Written Opinion", dated Oct. 17, 2019, 12 pages.
Previte et al., "DNA Sequencing using Polymerase Substrate-Binding Kinetics", Nature Communications, vol. 6, Jan. 23, 2015, pp. 1-12.

* cited by examiner

*Primary Examiner* — Teresa E Strzelecka
(74) *Attorney, Agent, or Firm* — Kilpatrick Townsend & Stockton LLP

(57) ABSTRACT

A method for identifying a nucleotide in a primed template nucleic acid, including the steps of (a) providing a vessel having a primed template nucleic acid, polymerase and a nucleotide cognate of a first base type; (b) examining the vessel for a stabilized ternary complex including the polymerase and the nucleotide cognate of the first base type bound at a base position of the primed template nucleic acid; (c) delivering a nucleotide cognate of a second base type to the vessel, whereby the vessel retains the primed template nucleic acid and the polymerase from step (b); (d) examining the vessel for a stabilized ternary complex including the polymerase and the nucleotide cognate of the second base type bound at the base position of the primed template nucleic acid; and (e) identifying the type of nucleotide at the base position of the primed template nucleic acid.

13 Claims, 3 Drawing Sheets

SERIAL FORMATION OF TERNARY COMPLEX SPECIES

CROSS-REFERENCE TO RELATED APPLICATIONS

This application is based on, and claims the benefit of, U.S. Provisional Application No. 62/702,468, filed Jul. 24, 2018, which is incorporated herein by reference in its entirety.

BACKGROUND

The present disclosure relates generally to detection of nucleic acids and has specific applicability to nucleic acid sequencing technology.

Accurate sequence determination of a template nucleic acid strand is important for molecular diagnostics. Identification of a single nucleotide base from among alternatives at a known position can serve as the basis for analysis of single nucleotide polymorphisms (i.e., "SNPs"). A SNP can in turn be used to determine a phenotype for the individual such as susceptibility to a disease or propensity for having a desirable trait. Detecting genetic variants in a patient can indicate the efficacy for certain medications to treat the patient or the risk of adverse side effects when treating the patient with certain medications.

Commercially available nucleic acid sequencing platforms have vastly increased our knowledge of the genetic underpinnings of actionable traits. Improvements in sequencing biochemistry and detection hardware continue. However, many platforms have achieved only relatively short reads. Massively parallel processing allows many short reads to be obtained and then knitted together to assemble a larger genomic sequence. For example, millions of reads that are each only a couple of hundred nucleotides in length can be assembled together to arrive at a human genome that is about 3 billion nucleotides long. The time and resources required to achieve massively parallel processing of the DNA and high throughput assembly of the data would be alleviated by increasing sequencing read-length. The present invention addresses this need and provides related advantages as well.

BRIEF SUMMARY

The present disclosure provides a method for identifying a nucleotide in a primed template nucleic acid. The method can include steps of (a) providing a vessel having a primed template nucleic acid, polymerase and a nucleotide cognate of a first base type; (b) examining the vessel for a stabilized ternary complex including the polymerase and the nucleotide cognate of the first base type bound at a base position of the primed template nucleic acid; (c) delivering a nucleotide cognate of a second base type to the vessel, whereby the vessel retains the primed template nucleic acid and the polymerase from step (b); (d) examining the vessel for a stabilized ternary complex including the polymerase and the nucleotide cognate of the second base type bound at the base position of the primed template nucleic acid; and (e) identifying the type of nucleotide at the base position of the primed template nucleic acid. Optionally, step (c) includes removing the nucleotide cognate of the first base type from the vessel and delivering the nucleotide cognate of the second base type to the vessel, whereby the vessel retains the primed template nucleic acid and the polymerase from step (b). As an alternative to this option the nucleotide cognate of the first base type need not be removed; and instead the vessel can retain the nucleotide cognate of the first base type in steps (c) and (d)

In some embodiments a method for identifying a nucleotide in a primed template nucleic acid can include steps of (a) providing a vessel having a primed template nucleic acid, polymerase and a nucleotide cognate of a first base type; (b) examining the vessel for a stabilized ternary complex including the polymerase and the nucleotide cognate of the first base type bound at a base position of the primed template nucleic acid; (c) delivering a nucleotide cognate of a second base type to the vessel, whereby the vessel retains the primed template nucleic acid and the polymerase from step (b); (d) examining the vessel for a stabilized ternary complex including the polymerase and the nucleotide cognate of the second base type bound at the base position of the primed template nucleic acid; (e) identifying the type of nucleotide at the base position of the primed template nucleic acid; (f) delivering a nucleotide cognate of a third base type to the vessel, whereby the vessel retains the primed template nucleic acid and the polymerase from step (b); and (g) examining the vessel for a stabilized ternary complex including the polymerase and the nucleotide cognate of the third base type bound at the base position of the primed template nucleic acid. Optionally, the method further includes steps of (h) delivering a nucleotide cognate of a fourth base type to the vessel, whereby the vessel retains the primed template nucleic acid and the polymerase from step (b); and (i) examining the vessel for a stabilized ternary complex including the polymerase and the nucleotide cognate of the fourth base type bound at the base position of the primed template nucleic acid.

The present disclosure provides a method for sequencing a primed template nucleic acid that includes steps of (a) providing a vessel having a primed template nucleic acid, first polymerase and a nucleotide cognate of a first base type; (b) examining the vessel for a stabilized ternary complex including the first polymerase and the nucleotide cognate of the first base type bound at a base position of the primed template nucleic acid; (c) delivering a nucleotide cognate of a second base type to the vessel, whereby the vessel retains the primed template nucleic acid and the first polymerase from step (b); (d) examining the vessel for a stabilized ternary complex including the first polymerase and the nucleotide cognate of the second base type bound at the base position of the primed template nucleic acid; (e) identifying the type of nucleotide at the base position of the primed template nucleic acid; (f) delivering a nucleotide cognate of a third base type to the vessel, whereby the vessel retains the primed template nucleic acid and the first polymerase from step (b); (g) examining the vessel for a stabilized ternary complex including the first polymerase and the nucleotide cognate of the third base type bound at the base position of the primed template nucleic acid; (h) delivering a nucleotide cognate of a fourth base type to the vessel, whereby the vessel retains the primed template nucleic acid and the first polymerase from step (b); (i) examining the vessel for a stabilized ternary complex including the first polymerase and the nucleotide cognate of the fourth base type bound at the base position of the primed template nucleic acid; (j) adding a nucleotide to the primer of the primed template nucleic acid, whereby the vessel comprises an extended primed template nucleic acid; (k) delivering a second polymerase and a nucleotide cognate of the first base type to the vessel; and (l) repeating steps (b) through (i) using the extended primed template instead of the primed template nucleic acid and using the second polymerase instead of the first polymerase. The first polymerase may be the same type of polymerase as the first type, or the first and second polymerase may be different types of polymerase.

A method for sequencing a primed template nucleic acid can include steps of (a) providing a vessel having a primed template nucleic acid, first polymerase and a nucleotide cognate of a first base type; (b) examining the vessel for a stabilized ternary complex including the first polymerase and the nucleotide cognate of the first base type bound at a base position of the primed template nucleic acid; (c) delivering a nucleotide cognate of a second base type to the vessel, whereby the vessel retains the primed template nucleic acid and the first polymerase from step (b); (d) examining the vessel for a stabilized ternary complex including the first polymerase and the nucleotide cognate of the second base type bound at the base position of the primed template nucleic acid; (e) identifying the type of nucleotide at the base position of the primed template nucleic acid; (f) adding a nucleotide to the primer of the primed template nucleic acid, whereby the vessel includes an extended primed template nucleic acid; (g) delivering a second polymerase and a nucleotide cognate of the first base type to the vessel; and (h) repeating steps (b) through (e) using the extended primed template instead of the primed template nucleic acid and using the second polymerase instead of the first polymerase. The first polymerase may be the same type of polymerase as the first type, or the first and second polymerase may be different types of polymerase.

The present disclosure further provides a method for identifying a nucleotide in a primed template nucleic acid, that includes steps of (a) providing an array of primed template nucleic acids; (b) forming stabilized ternary complexes each including a polymerase, a nucleotide cognate of a first base type and a primed template nucleic acid in the array; (c) detecting the stabilized ternary complexes in the array; (d) repeating steps (b) and (c) for a nucleotide cognate of a second base type, whereby the primed template nucleic acids and the polymerases are retained in the array; and (e) identifying the type of nucleotide that is present in each of the stabilized ternary complexes detected in step (c). Optionally, step (d) includes removing the nucleotide cognate of the first base type from the array and then repeating steps (b) and (c) for a nucleotide cognate of a second base type, whereby the primed template nucleic acids and the polymerases are retained in the array. As an alternative to this option the nucleotide cognate of the first base type need not be removed; and instead the nucleotide cognate of the first base type can be retained with the array in step (d).

In some embodiments, a method for identifying a nucleotide in a primed template nucleic acid can include steps of (a) providing an array of primed template nucleic acids; (b) forming stabilized ternary complexes each including a polymerase, a nucleotide cognate of a first base type and a primed template nucleic acid in the array; (c) detecting the stabilized ternary complexes in the array; (d) repeating steps (b) and (c) for a nucleotide cognate of a second base type, whereby the primed template nucleic acids and the polymerases are retained in the array; and (e) identifying the type of nucleotide that is present in each of the stabilized ternary complexes detected in step (c). Optionally, step (d) is carried out by repeating steps (b) and (c) for the nucleotide cognate of the second base type, and then repeating steps (b) and (c) for a nucleotide cognate of a third base type. Further optionally, step (d) is carried out by repeating steps (b) and (c) for the nucleotide cognate of the second base type, then repeating steps (b) and (c) for the nucleotide cognate of the third base type and then repeating steps (b) and (c) for a nucleotide cognate of a fourth base type.

Also provided is a method for sequencing primed template nucleic acids, that includes steps of (a) providing an array of primed template nucleic acids; (b) forming stabilized ternary complexes each including a first polymerase, a nucleotide cognate of a first base type and a primed template nucleic acid in the array; (c) detecting the stabilized ternary complexes in the array; (d) repeating steps (b) and (c) for a nucleotide cognate of a second base type, then repeating steps (b) and (c) for the nucleotide cognate of the third base type and then repeating steps (b) and (c) for a nucleotide cognate of a fourth base type, whereby the primed template nucleic acids and the first polymerases are retained in the array; (e) identifying the type of nucleotide that is present in each of the stabilized ternary complexes detected in step (c); (f) adding a nucleotide to the primer of each of the primed template nucleic acids, whereby the array includes extended primed template nucleic acids; and (g) repeating steps (b) through (e) using the extended primed template instead of the primed template nucleic acid and using a second polymerase instead of the first polymerase. The first polymerase may be the same type of polymerase as the first type, or the first and second polymerase may be different types of polymerase.

A method for sequencing primed template nucleic acids can include steps of (a) providing an array of primed template nucleic acids; (b) forming stabilized ternary complexes each including a first polymerase, a nucleotide cognate of a first base type and a primed template nucleic acid in the array; (c) detecting the stabilized ternary complexes in the array; (d) repeating steps (b) and (c) for a nucleotide cognate of a second base type, whereby the primed template nucleic acids and the first polymerases are retained in the array; (e) identifying the type of nucleotide that is present in each of the stabilized ternary complexes detected in step (c); (f) adding a nucleotide to the primer of each of the primed template nucleic acids, whereby the array includes extended primed template nucleic acids; and (g) repeating steps (b) through (e) using the extended primed template instead of the primed template nucleic acid and using a second polymerase instead of the first polymerase. The first polymerase may be the same type of polymerase as the first type, or the first and second polymerase may be different types of polymerase.

The present disclosure further provides a method for identifying a nucleotide in a primed template nucleic acid, that includes steps of (a) providing an array of primed template nucleic acids; (b) delivering a plurality of polymerases and a plurality of nucleotide cognates of a first base type to the array, thereby forming stabilized ternary complexes each including a polymerase of the plurality of polymerases, a nucleotide of the plurality of nucleotide cognates of the first base type and a primed template nucleic acid of the array; (c) detecting the stabilized ternary complexes in the array; (d) repeating steps (b) and (c) for nucleotide cognates of a second base type, whereby primed template nucleic acids of the array and polymerases of the plurality of polymerases are retained in the array; and (e) identifying the type of nucleotide that is present in each of the stabilized ternary complexes detected in step (c). Optionally, step (d) includes removing the plurality of nucleotide cognates of the first base type from the array and then repeating steps (b) and (c) for nucleotide cognates of a second base type, whereby primed template nucleic acids of the array and the polymerases of the plurality of polymerases are retained in the array. As an alternative to this option nucleotide cognates of the first base type need not be removed; and instead nucleotides of the plurality of nucleotide cognates of the first base type can be retained with the array in step (d).

Also provided is a method for identifying a nucleotide in a primed template nucleic acid, that includes steps of (a) providing an array of primed template nucleic acids; (b) delivering a plurality of polymerases and a plurality of nucleotide cognates of a first base type to the array, thereby forming stabilized ternary complexes each including a polymerase of the plurality of polymerases, a nucleotide of the plurality of nucleotide cognates of the first base type and a primed template nucleic acid of the array; (c) detecting the stabilized ternary complexes in the array; (d) repeating steps (b) and (c) for nucleotide cognates of a second base type, whereby primed template nucleic acids of the array and polymerases of the plurality of polymerases are retained in the array; and (e) identifying the type of nucleotide that is present in each of the stabilized ternary complexes detected in step (c). Optionally, step (d) is carried out by repeating steps (b) and (c) for the nucleotide cognates of the second base type, and then repeating steps (b) and (c) for nucleotide cognates of a third base type. Further optionally, step (d) is carried out by repeating steps (b) and (c) for the nucleotide cognates of the second base type, then repeating steps (b) and (c) for the nucleotide cognates of the third base type and then repeating steps (b) and (c) for nucleotide cognates of a fourth base type.

Also provided is a method for sequencing primed template nucleic acids, that includes steps of (a) providing an array of primed template nucleic acids; (b) delivering a plurality of polymerases and a plurality of nucleotide cognates of a first base type to the array, thereby forming stabilized ternary complexes each including a polymerase of the plurality of polymerases, a nucleotide of the plurality of nucleotide cognates of the first base type and a primed template nucleic acid of the array; (c) detecting the stabilized ternary complexes in the array; (d) repeating steps (b) and (c) for nucleotide cognates of a second base type, then repeating steps (b) and (c) for the nucleotide cognates of the third base type and then repeating steps (b) and (c) for nucleotide cognates of a fourth base type, whereby primed template nucleic acids of the array and polymerases of the plurality of polymerases are retained in the array; (e) identifying the type of nucleotide that is present in each of the stabilized ternary complexes detected in step (c); (f) adding a nucleotide to the primer of each of the primed template nucleic acids, whereby the array includes extended primed template nucleic acids; and (g) repeating steps (b) through (e) using the extended primed template instead of the primed template nucleic acids and using a plurality of second polymerases instead of the plurality of polymerases.

A method for sequencing primed template nucleic acids can include steps of (a) providing an array of primed template nucleic acids; (b) delivering a plurality of polymerases and a plurality of nucleotide cognates of a first base type to the array, thereby forming stabilized ternary complexes each including a polymerase of the plurality of polymerases, a nucleotide of the plurality of nucleotide cognates of the first base type and a primed template nucleic acid of the array; (c) detecting the stabilized ternary complexes in the array; (d) repeating steps (b) and (c) for nucleotide cognates of a second base type, whereby primed template nucleic acids of the array and polymerases of the plurality of polymerases are retained in the array; (e) identifying the type of nucleotide that is present in each of the stabilized ternary complexes detected in step (c); (f) adding a nucleotide to the primer of each of the primed template nucleic acids, whereby the array includes extended primed template nucleic acids; and (g) repeating steps (b) through (e) using the extended primed template instead of the primed template nucleic acids and using a plurality of second polymerases instead of the plurality of polymerases.

Also provided is a method for identifying a nucleotide in a primed template nucleic acid that includes steps of (a) providing an array of primed template nucleic acids; (b) delivering a plurality of nucleotide cognates of a first base type and a plurality of polymerases to the array, thereby forming stabilized ternary complexes each including a polymerase of the plurality of polymerases, a nucleotide of the plurality of nucleotide cognates of the first base type and a primed template nucleic acid in the array; (c) detecting the stabilized ternary complexes in the array that include the nucleotide cognates of the first base type; (d) delivering a plurality of nucleotide cognates of a second base type to the array in the presence of polymerases from step (b), thereby forming stabilized ternary complexes each including a polymerase of the polymerases from step (b), a nucleotide of the plurality of nucleotide cognates of the second base type and a primed template nucleic acid in the array; (e) detecting the stabilized ternary complexes in the array that include the nucleotide cognates of the second base type; and (f) identifying the type of nucleotide that is present in each of the stabilized ternary complexes detected in step (c). Optionally, the method further includes repeating steps (d) and (e) using nucleotide cognates of a third base type instead of the nucleotide cognates of the second base type. As another option, the method can further include repeating steps (d) and (e) using nucleotide cognates of a fourth base type instead of the nucleotide cognates of the second base type. In a further option, the method can include steps of (g) adding a nucleotide to the primer of each of the primed template nucleic acids, whereby the array includes extended primed template nucleic acids; and (h) repeating steps (b) through (f) using the extended primed templates instead of the primed template nucleic acids.

DETAILED DESCRIPTION

Figure 1:
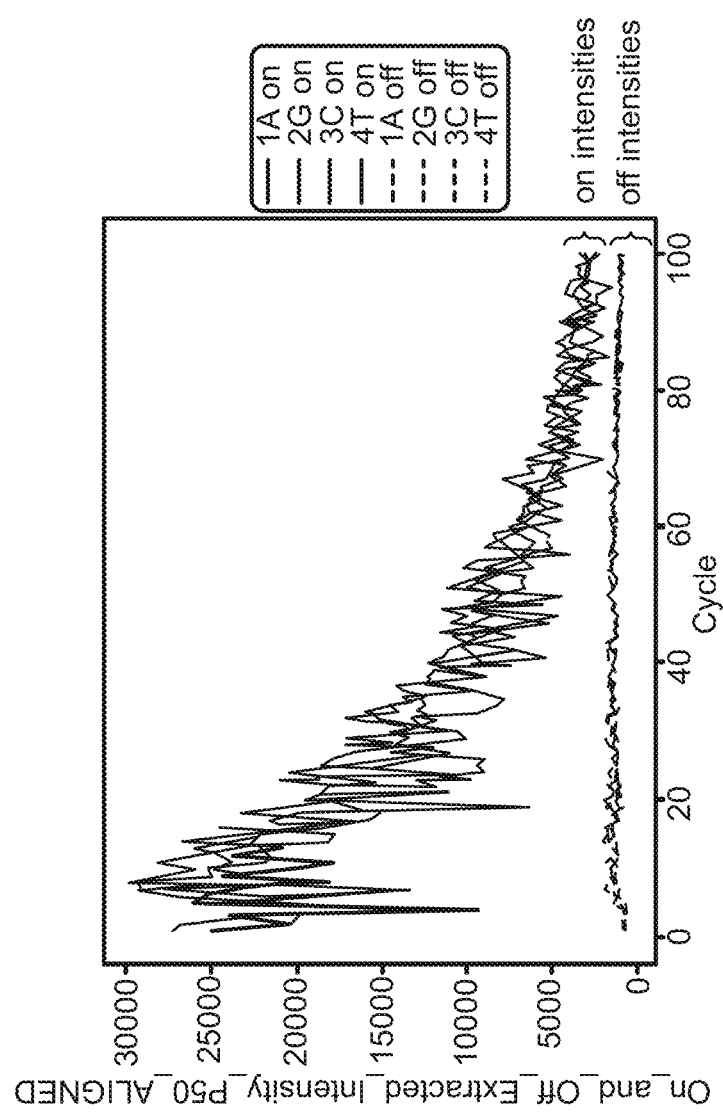
FIG. 1 shows a plot of 'on' signal intensity (corresponds to the binding of the cognate nucleotide) and 'off' signal intensity (corresponds to the binding of the non-cognate nucleotide) vs. sequencing cycle for a sequencing protocol that includes steps of washing primed template nucleic acids to replace polymerase and nucleotides between examination steps.

The present disclosure provides methods for identifying a nucleotide in a primed template nucleic acid. The nucleotide is identified based on formation of a ternary complex that includes the primed template nucleic acid, a polymerase that binds to the template at the 3' end of the primer and a cognate nucleotide that binds to the polymerase to pair with a nucleotide in the template that is adjacent to the 3' end of the primer. A variety of different nucleotide types can be evaluated for the ability to form a ternary complex. The type of nucleotide that is observed to participate in formation of a ternary complex can be identified as the cognate nucleotide for the template position that is being queried. Based on this observation and the known rules for pairing nucleotides (i.e. adenine pairs with thymine or uracil, and cytosine pairs with guanine), the nucleotide type at the template position can be inferred.

A useful method for querying the primed template nucleic acid is to deliver a polymerase and a first type of nucleotide to an immobilized nucleic acid, examine the solid support for recruitment of the ternary complex components to the immobilized nucleic acid, remove the polymerase and nucleotide from the solid support to which the nucleotide is immobilized, and then repeat the cycle for a different type of nucleotide. Although this method is useful for characterizing the nucleic acid, the delivery and removal of reagents from the solid support can be time consuming. Moreover, this replacement cycle consumes a relatively large amount of polymerase, which can be an expensive reagent to produce.

The present disclosure provides a method whereby different nucleotide types are serially delivered and then removed from a vessel where ternary complex is to be formed and examined. In this mode, a first nucleotide type can be delivered to a reaction vessel and then removed from the vessel prior to delivering a second nucleotide type to the vessel. A nucleotide cognate can be removed from a vessel under conditions that will dissociate the nucleotide from a ternary complex, thereby allowing the nucleotide to be separated from the primed template nucleic acid without causing substantial removal of the polymerase. Another nucleotide can then be delivered to the primed template nucleic acid. Delivery of more polymerase is not necessary if the polymerase is not substantially removed from the presence of the primed template nucleic acid. This provides a savings of time and resources that would otherwise be spent preparing more polymerase.

In other embodiments, different nucleotide types can be serially delivered to a vessel containing one or more primed template nucleic acids under conditions that are amenable to formation of ternary complex. For example, a first nucleotide type can be delivered to a vessel that contains an array of primed template nucleic acids and then a second nucleotide type can be delivered, such that the two nucleotide types accumulate in the vessel. As such, two types of ternary complexes, each containing one of the two different nucleotide types, can accumulate in the array. Optionally, at least 2, 3 or 4 different nucleotide types can accumulate in the array to form at least 2, 3, or 4 different types of ternary complex on the array. When performing the methods in a mode whereby different nucleotide types are serially delivered to a reaction vessel such that the different nucleotides accumulate, examination of the vessel for ternary complexes can be carried out after each delivery. In some embodiments, for example when each nucleotide type is distinguishably labeled, a single examination can occur after all nucleotides have been delivered.

In particular embodiments a primer extension step can be added to advance to the next template position for subsequent examination. Detection of a series of positions in a region of the template can be used to determine the nucleotide sequence for that region. As set forth in the Example section below, the above embodiments surprisingly, provide improved sequencing accuracy and read length when employed in a Sequencing By Binding™ protocol.

Although the embodiments above are exemplified for delivery of a single type of nucleotide in each step, it will be understood that multiple nucleotide types can be delivered in one or more step. The nucleotides can be distinguished, for example, using different labels attached to each type of nucleotide, respectively. Mixtures of nucleotides can differ from each other such that the net result of the different deliveries and examinations is to produce a series of signals that encode a particular nucleotide type. Exemplary encoding schemes and mixtures of nucleotides that can be used to produce the codes are set forth in U.S. Pat. No. 9,951,385 and U.S. patent application Ser. No. 15/922,787, now granted as U.S. Pat. No. 10,161,003, each of which is incorporated herein by reference.

Terms used herein will be understood to take on their ordinary meaning in the relevant art unless specified otherwise. Several terms used herein, and their meanings, are set forth below.

As used herein, the term "array" refers to a population of molecules attached to one or more solid support such that the molecules at one feature can be distinguished from molecules at other features. An array can include different molecules that are each located at different addressable features on a solid support. Alternatively, an array can include separate solid supports each functioning as a feature that bears a different molecule, wherein the different molecules can be identified according to the locations of the solid supports on a surface to which the solid supports are attached, or according to the locations of the solid supports in a liquid such as a fluid stream. The molecules of the array can be, for example, nucleotides, nucleic acid primers, nucleic acid templates, primed template nucleic acids, or nucleic acid enzymes such as polymerases, ligases, exonucleases or combinations thereof.

As used herein, the term "blocking moiety," when used in reference to a nucleotide, means a part of the nucleotide that inhibits or prevents the 3' oxygen of the nucleotide from forming a covalent linkage to a next correct nucleotide during a nucleic acid polymerization reaction. The blocking moiety of a "reversibly terminated" nucleotide can be removed from the nucleotide analog, or otherwise modified, to allow the 3'-oxygen of the nucleotide to covalently link to a next correct nucleotide. Such a blocking moiety is referred to herein as a "reversible terminator moiety." Exemplary reversible terminator moieties are set forth in U.S. Pat. Nos. 7,427,673; 7,414,116; 7,057,026; 7,544,794 or 8,034,923; or PCT publications WO 91/06678 or WO 07/123744, each of which is incorporated herein by reference. A nucleotide that has a blocking moiety or reversible terminator moiety can be at the 3' end of a nucleic acid, such as a primer, or can be a monomer that is not covalently attached to a nucleic acid. A particularly useful blocking moiety will be present at the 3' end of a nucleic acid that participates in formation of a ternary complex.

As used herein, the term "catalytic metal ion" refers to a metal ion that facilitates phosphodiester bond formation between the 3'-oxygen of a nucleic acid (e.g., a primer) and the phosphate of an incoming nucleotide by a polymerase. A "divalent catalytic metal cation" is a catalytic metal ion having a valence of two. Catalytic metal ions can be present at concentrations that stabilize formation of a complex between a polymerase, nucleotide, and primed template nucleic acid, referred to as non-catalytic concentrations of a metal ion insofar as phosphodiester bond formation does not occur. Catalytic concentrations of a metal ion refer to the amount of a metal ion sufficient for polymerases to catalyze the reaction between the 3'-oxygen of a nucleic acid (e.g., a primer) and the phosphate group of an incoming nucleotide.

As used herein, the term "binary complex" refers to an intermolecular association between a polymerase and a primed template nucleic acid, exclusive of a nucleotide molecule such as a next correct nucleotide of the primed template nucleic acid.

The term "comprising" is intended herein to be open-ended, including not only the recited elements, but further encompassing any additional elements.

As used herein, the term "deblock" means to remove or modify a reversible terminator moiety of a nucleotide to render the nucleotide extendable. For example, the nucleotide can be present at the 3' end of a primer such that deblocking renders the primer extendable. Exemplary deblocking reagents and methods are set forth in U.S. Pat. Nos. 7,427,673; 7,414,116; 7,057,026; 7,544,794 or 8,034,923; or PCT publications WO 91/06678 or WO 07/123744, each of which is incorporated herein by reference.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous label that is present on a polymerase is not found on the polymerase in its native milieu.

As used herein, the term "extension," when used in reference to a nucleic acid, means a process of adding at least one nucleotide to the 3' end of the nucleic acid. The term "polymerase extension," when used in reference to a nucleic acid, refers to a polymerase catalyzed process of adding at least one nucleotide to the 3' end of the nucleic acid. A nucleotide or oligonucleotide that is added to a nucleic acid by extension is said to be incorporated into the nucleic acid. Accordingly, the term "incorporating" can be used to refer to the process of joining a nucleotide or oligonucleotide to the 3' end of a nucleic acid by formation of a phosphodiester bond.

As used herein, the term "extendable," when used in reference to a nucleotide, means that the nucleotide has an oxygen or hydroxyl moiety at the 3' position, and is capable of forming a covalent linkage to a next correct nucleotide if and when incorporated into a nucleic acid. An extendable nucleotide can be at the 3' position of a primer or it can be a monomeric nucleotide. A nucleotide that is extendable will lack blocking moieties such as reversible terminator moieties.

As used herein, the term "feature," when used in reference to an array, means a location in an array where a particular molecule is present. A feature can contain only a single molecule or it can contain a population of several molecules of the same species (i.e. an ensemble of the molecules). Alternatively, a feature can include a population of molecules that are different species (e.g. a population of ternary complexes having different template sequences). Features of an array are typically discrete. The discrete features can be contiguous or they can have spaces between each other. An array useful herein can have, for example, features that are separated by less than 100 microns, 50 microns, 10 microns, 5 microns, 1 micron, or 0.5 micron. Alternatively or additionally, an array can have features that are separated by greater than 0.5 micron, 1 micron, 5 microns, 10 microns, 50 microns or 100 microns. The features can each have an area of less than 1 square millimeter, 500 square microns, 100 square microns, 25 square microns, 1 square micron or less.

As used herein, a "flow cell" is a reaction chamber that includes one or more channels that direct fluid to a detection zone. The detection zone can be coupled to a detector such that a reaction occurring in the reaction chamber can be observed. For example, a flow cell can contain primed template nucleic acid molecules tethered to a solid support, to which nucleotides and ancillary reagents are iteratively applied and washed away. The flow cell can include a transparent material that permits the sample to be imaged after a desired reaction occurs. For example, a flow cell can include a glass or plastic slide containing small fluidic channels through which polymerases, dNTPs and buffers can be pumped. The glass or plastic inside the channels can be decorated with one or more primed template nucleic acid molecules to be sequenced. An external imaging system can be positioned to detect the molecules at a detection zone. Exemplary flow cells, methods for their manufacture and methods for their use are described in US Pat. App. Publ. Nos. 2010/0111768 A1 or 2012-0270305 A1; or WO 05/065814, each of which is incorporated by reference herein.

As used herein, the term "label" refers to a molecule, or moiety thereof, that provides a detectable characteristic. The detectable characteristic can be, for example, an optical signal such as absorbance of radiation, fluorescence emission, luminescence emission, fluorescence lifetime, fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like.

As used herein, the term "next correct nucleotide" refers to the nucleotide type that will bind and/or incorporate at the 3' end of a primer to complement a base in a template strand to which the primer is hybridized. The base in the template strand is referred to as the "next base" and is immediately 5' of the base in the template that is hybridized to the 3' end of the primer. The next correct nucleotide can be referred to as the "cognate" of the next base and vice versa. Cognate nucleotides that interact with each other in a ternary complex or in a double stranded nucleic acid are said to "pair" with each other. In accordance with Watson-Crick pairing rules adenine (A) pairs with thymine (T) or uracil (U), and cytosine (C) pairs with guanine (G). A nucleotide having a base that is not complementary to the next template base is referred to as an "incorrect", "mismatch" or "non-cognate" nucleotide.

As used herein, the term "non-catalytic metal ion" refers to a metal ion that, when in the presence of a polymerase enzyme, does not facilitate phosphodiester bond formation needed for chemical incorporation of a nucleotide into a primer. A non-catalytic metal ion may interact with a polymerase, for example, via competitive binding compared to catalytic metal ions. Accordingly, a non-catalytic metal ion can act as an inhibitory metal ion. A "divalent non-catalytic metal ion" is a non-catalytic metal ion having a valence of two. Examples of divalent non-catalytic metal ions include, but are not limited to, $Ca^{2-}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein, the term "nucleotide" can be used to refer to a native nucleotide or analog thereof. Examples include, but are not limited to, nucleotide triphosphates (NTPs) such as ribonucleotide triphosphates (rNTPs), deoxyribonucleotide triphosphates (dNTPs), or non-natural analogs thereof such as dideoxyribonucleotide triphosphates (ddNTPs) or reversibly terminated nucleotide triphosphates (rtNTPs).

As used herein, the term "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' oxygen group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, the term "primed template nucleic acid" or "primed template" refers to a nucleic acid having a double stranded region such that one of the strands is a primer and the other strand is a template. The two strands can be parts of a contiguous nucleic acid molecule (e.g. a hairpin structure) or the two strands can be separable molecules that are not covalently attached to each other.

As used herein, the term "primer" refers to a nucleic acid having a sequence that binds to a nucleic acid at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence. A primer can consist of DNA, RNA or analogs thereof. A primer can have an extendible 3' end or a 3' end that is blocked from primer extension.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, the term "type" is used to identify molecules that share the same chemical structure. For example, a mixture of nucleotides can include several dCTP molecules. The dCTP molecules will be understood to be the same type of nucleotide as each other, but a different type of nucleotide compared to dATP, dGTP, dTTP etc. Similarly, individual DNA molecules that have the same sequence of nucleotides are the same type, whereas DNA molecules with different sequences are different types. The term "type" can also identify moieties that share the same chemical structure. For example, the cytosine bases in a template nucleic acid will be understood to be the same type of base as each other independent of their position in the template sequence.

As used herein, a "vessel" is a container that functions to isolate one chemical process (e.g., a binding event; an incorporation reaction; etc.) from another, or to provide a space in which a chemical process can take place. Non-limiting examples of vessels useful in connection with the disclosed technique include: flow cells, wells of a multi-well plate; microscope slides; tubes (e.g., capillary tubes); droplets, vesicles, test tubes, trays, centrifuge tubes, features in an array, tubing, channels in a substrate etc. As used herein, a "manufactured vessel" is a container that is human-made or human-modified and that functions to isolate one chemical process (e.g., a binding event; an incorporation reaction; etc.) from another, or to provide a space in which a chemical process can take place.

The embodiments set forth below and recited in the claims can be understood in view of the above definitions.

The present disclosure provides a method for identifying a nucleotide in a primed template nucleic acid. The method can include steps of (a) providing a vessel having a primed template nucleic acid, polymerase and a nucleotide cognate of a first base type; (b) examining the vessel for a stabilized ternary complex including the polymerase and the nucleotide cognate of the first base type bound at a base position of the primed template nucleic acid; (c) delivering a nucleotide cognate of a second base type to the vessel, whereby the vessel retains the primed template nucleic acid and the polymerase from step (b); (d) examining the vessel for a stabilized ternary complex including the polymerase and the nucleotide cognate of the second base type bound at the base position of the primed template nucleic acid; and (e) identifying the type of nucleotide at the base position of the primed template nucleic acid.

Also provided is a method for identifying a nucleotide in a primed template nucleic acid, that includes steps of (a) providing an array of primed template nucleic acids; (b) forming stabilized ternary complexes each including a polymerase, a nucleotide cognate of a first base type and a primed template nucleic acid in the array; (c) detecting the stabilized ternary complexes in the array; (d) repeating steps (b) and (c) for a nucleotide cognate of a second base type, whereby the primed template nucleic acids and the polymerases are retained in the array; and (e) identifying the type of nucleotide that is present in each of the stabilized ternary complexes detected in step (c).

The present disclosure further provides a method for identifying a nucleotide in a primed template nucleic acid, that includes steps of (a) providing an array of primed template nucleic acids; (b) delivering a plurality of polymerases and a plurality of nucleotide cognates of a first base type to the array, thereby forming stabilized ternary complexes each including a polymerase of the plurality of polymerases, a nucleotide of the plurality of nucleotide cognates of the first base type and a primed template nucleic acid of the array; (c) detecting the stabilized ternary complexes in the array; (d) repeating steps (b) and (c) for nucleotide cognates of a second base type, whereby primed template nucleic acids of the array and polymerases of the plurality of polymerases are retained in the array; and (e) identifying the type of nucleotide that is present in each of the stabilized ternary complexes detected in step (c).

A method of this disclosure can include an examination step for detecting a ternary complex. Embodiments of the methods exploit the specificity with which a polymerase can form a stabilized ternary complex with a primed template nucleic acid and a next correct nucleotide. The next correct nucleotide can be non-covalently bound to the stabilized ternary complex, interacting with the other members of the complex solely via non-covalent interactions. Useful methods and compositions for forming a stabilized ternary complex are set forth in further detail below and in commonly owned U.S. Pat. App. Pub. No. 2017/0022553 A1 or U.S. patent application Ser. No. 15/677,870, published as U.S. Pat. App. Pub. No. 2018/0044727 A1; U.S. patent application Ser. No. 15/851,383 which is published as U.S. Pat. App. Pub. No. 2018/0187245 A1 and claims priority to U.S. Pat. App. Ser. No. 62/440,624 or U.S. patent application Ser. No. 15/873,343 which is published as U.S. Pat. App. Pub. No. 2018/0208983 A1 and claims priority to U.S. Pat. App. Ser. No. 62/450,397, each of which is incorporated herein by reference.

Typically, examination is carried out separately and discretely from primer extension, for example, due to a reagent exchange or wash that intervenes examination and extension. Alternatively, examination and primer extension steps can occur in the same mixture in some embodiments.

While a ternary complex can form between a polymerase, primed template nucleic acid and next correct nucleotide in the absence of certain catalytic metal ions (e.g., $Mg^{2+}$), chemical addition of the nucleotide is inhibited in the absence of the catalytic metal ions. Low or deficient levels of catalytic metal ions, cause non-covalent sequestration of the next correct nucleotide in a stabilized ternary complex. Other methods disclosed herein also can be used to produce a stabilized ternary complex.

Optionally, a stabilized ternary complex can be formed when the primer of the primed template nucleic acid includes a blocking moiety (e.g. a reversible terminator moiety) that precludes enzymatic incorporation of an incoming nucleotide into the primer. The interaction can take place in the presence of stabilizers, whereby the polymerase-nucleic acid interaction is stabilized in the presence of the next correct nucleotide. The primer of the primed template nucleic acid optionally can be either an extendable primer, or a primer blocked from extension at its 3'-end (e.g., blocking can be achieved by the presence of a reversible terminator moiety on the 3'-end of the primer). The primed template nucleic acid, the polymerase and the cognate nucleotide are capable of forming a stabilized ternary complex when the base of the next correct nucleotide is complementary to the next base of the primed template nucleic acid.

As set forth above, conditions that favor or stabilize a ternary complex can be provided by the presence of a blocking group that precludes enzymatic incorporation of an incoming nucleotide into the primer (e.g. a reversible terminator moiety on the 3' nucleotide of the primer) or by the absence of a catalytic metal ion. Other useful conditions include the presence of a ternary complex stabilizing agent such as a non-catalytic ion (e.g., a divalent or trivalent non-catalytic metal ion) that inhibits nucleotide incorporation or polymerization. Non-catalytic metal ions include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, conditions that disfavor or destabilize binary complexes (i.e. complexes between polymerase and primed nucleic acid but lacking cognate nucleotide) are provided by the presence of one or more monovalent cations and/or glutamate anions. As a further option, a polymerase engineered to prevent catalytic activity or to prevent propensity for binary complex formation can be used.

Ternary complex stabilization conditions can be further formulated to accentuate the difference in affinity of polymerase toward primed template nucleic acids in the presence of different nucleotides, for example, by destabilizing binary complexes. Optionally, the conditions cause differential affinity of the polymerase for the primer-template in the presence of different nucleotides. By way of example, the conditions include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate ions. Optionally, the source of glutamate ions can be potassium glutamate. In some instances, the concentrations of potassium glutamate that can be used to alter polymerase affinity of the primer-template hybrid extend from 10 mM to 1.6 M of potassium glutamate, or any amount in between 10 mM and 1.6 M. As indicated above, high salt refers to a concentration of salt from 50 mM to 1.5 M salt.

It will be understood that options set forth herein for stabilizing a ternary complex need not be mutually exclusive and instead can be used in various combinations. For example, a ternary complex can be stabilized by one or a combination of means including, but not limited to, crosslinking of the polymerase domains, crosslinking of the polymerase to the nucleic acid, polymerase mutations that stabilize the ternary complex, allosteric inhibition by small molecules, uncompetitive inhibitors, competitive inhibitors, non-competitive inhibitors, absence of catalytic metal ions, presence of a blocking moiety on the primer, and other means set forth herein. In particular configurations of the methods or compositions set forth herein, the polymerase is not covalently attached to other components of the ternary complex that the polymerase participates in. Moreover, the polymerase need not be covalently attached to any solid phase material, such as a substrate used for an array of nucleic acids. Rather, the polymerase can be free to diffuse in solution but for its non-covalent affinity for components of the ternary complex that are attached to a substrate such as a feature of an array of nucleic acids.

A stabilized ternary complex can include a native nucleotide, nucleotide analog or modified nucleotide as desired to suit a particular application or configuration of the methods.

Optionally, a nucleotide analog has a nitrogenous base, five-carbon sugar, and phosphate group, wherein any moiety of the nucleotide may be modified, removed and/or replaced as compared to a native nucleotide. Nucleotide analogs may be non-incorporable nucleotides (i.e. nucleotides that are incapable of reacting with the 3' oxygen of a primer to form a covalent linkage). Such nucleotides that are incapable of incorporation include, for example, monophosphate and diphosphate nucleotides. In another example, the nucleotide may contain modification(s) at the 5' position (e.g. at the triphosphate group) that make the nucleotide non-incorporable. Examples of non-incorporable nucleotides may be found in U.S. Pat. No. 7,482,120, which is incorporated by reference herein. In some embodiments, non-incorporable nucleotides may be subsequently modified to become incorporable. Non-incorporable nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, nucleotides having a 5' phosphorothioate moiety, or caged nucleotides. Examples of nucleotide analogs are described in U.S. Pat. No. 8,071,755, which is incorporated by reference herein. Nucleotide analogs that participate in stabilized ternary complexes can include terminators that reversibly prevent subsequent nucleotide incorporation at the 3'-end of the primer after the analog has been incorporated into the primer. For example, U.S. Pat. Nos. 7,544,794 and 8,034,923 (the disclosures of these patents are incorporated herein by reference) describe reversible terminators in which the 3'-OH group is replaced by a 3'-ONH$_2$ moiety. Another type of reversible terminator is linked to the nitrogenous base of a nucleotide as set forth, for example, in U.S. Pat. No. 8,808,989 (the disclosure of which is incorporated herein by reference). Other reversible terminators that similarly can be used in connection with the methods described herein include an azido methyl moiety or others described in references cited elsewhere herein or in U.S. Pat. Nos. 7,956,171, 8,071,755, and 9,399,798 (the disclosures of these U.S. patents are incorporated herein by reference). In certain embodiments, a reversible terminator moiety can be modified or removed from a primer, in a process known as "deblocking," allowing for subsequent nucleotide incorporation. Compositions and methods for deblocking are set forth in references cited herein in the context of reversible terminators.

Alternatively, nucleotide analogs irreversibly prevent nucleotide incorporation at the 3'-end of the primer to which they have been incorporated. Irreversible nucleotide analogs include 2', 3'-dideoxynucleotides (ddNTPs such as ddGTP, ddATP, ddTTP, ddCTP). Dideoxynucleotides lack the 3'-OH group of dNTPs that would otherwise participate in polymerase-mediated primer extension. Thus, the 3' position has a hydrogen moiety instead of the native hydroxyl moiety. Irreversibly terminated nucleotides can be particularly useful for genotyping applications or other applications where primer extension or sequential detection along a template nucleic acid is not desired.

In some embodiments, a nucleotide that participates in forming a ternary complex can include an exogenous label such as a luminophore. Optionally, an exogenously labeled nucleotide can include a reversible or irreversible terminator moiety, an exogenously labeled nucleotide can be non-incorporable, an exogenously labeled nucleotide can lack blocking moieties, an exogenously labeled nucleotide can be incorporable or an exogenously labeled nucleotide can be both incorporable and non-terminated. Exogenously labeled nucleotides can be particularly useful when used to form a stabilized ternary complex with a non-labeled polymerase. For example, the label can produce luminescence that is detected in a method set forth herein. Alternatively, an exogenous label on a nucleotide can provide one partner in a fluorescence resonance energy transfer (FRET) pair and an exogenous label on a polymerase can provide the second partner of the pair. As such, FRET detection can be used to identify a stabilized ternary complex that includes both partners. Alternatively, a nucleotide that participates in forming a ternary complex can lack exogenous labels (i.e. the nucleotide can be "non-labeled"). Optionally, a non-labeled nucleotide can include a reversible or irreversible terminator moiety, a non-labeled nucleotide can be non-incorporable, a non-labeled nucleotide can lack terminator moieties, a non-labeled nucleotide can be incorporable, or a non-labeled nucleotide can be both incorporable and non-terminated. Non-labeled nucleotides can be useful when a label on a polymerase is used to detect a stabilized ternary complex. Non-labeled nucleotides can also be useful in an extension step of a method set forth herein. It will be understood that absence of a moiety or function for a nucleotide refers to the nucleotide having no such function or moiety. It will also be understood that one or more of the functions or moieties set forth herein for a nucleotide, or analog thereof, or otherwise known in the art for a nucleotide, or analog thereof, can be specifically omitted in a method or composition set forth herein.

Optionally, a nucleotide (e.g. a native nucleotide or synthetic nucleotide analog) is present in a mixture during formation of a stabilized ternary complex. For example, at least 1, 2, 3, 4 or more nucleotide types can be present. Alternatively or additionally, at most 4, 3, 2, or 1 nucleotide types can be present. Similarly, one or more nucleotide types that are present can be complementary to at least 1, 2, 3 or 4 base types in a template nucleic acid. Alternatively or additionally, one or more nucleotide types that are present can be complementary to at most 4, 3, 2, or 1 base types in a template nucleic acid.

Any nucleotide modification that does not prevent participation in a ternary complex may be used in the methods disclosed herein. The nucleotide may be bound permanently or transiently to a polymerase. Optionally, a nucleotide analog is fused to a polymerase, for example, via a covalent linker. Optionally, a plurality of nucleotide analogs is fused to a plurality of polymerases, wherein each nucleotide analog is fused to a different polymerase. Optionally, a nucleotide that is present in a stabilized ternary complex is not the means by which the ternary complex is stabilized. Accordingly, any of a variety of other ternary complex stabilization methods may be combined in a reaction utilizing a nucleotide analog.

In particular embodiments, the primer strand of a primed template nucleic acid molecule that is present in a stabilized ternary complex is chemically unchanged by a polymerase that is present during one or more steps of a method set forth herein. For example, the primer need not be extended by formation of a new phosphodiester bond, nor shortened by nucleolytic degradation during a step for forming a stabilized ternary complex, nor during a step for detecting the stabilized ternary complex.

A ternary complex that is made or used in accordance with the present disclosure may optionally include one or more exogenous label(s). The label can be attached to a component of the ternary complex (e.g. attached to the polymerase, template nucleic acid, primer and/or cognate nucleotide) prior to formation of the ternary complex. Exemplary attachments include covalent attachments or non-covalent attachments such as those set forth herein, in references cited herein or known in the art. In some embodiments, a labeled component is delivered in solution to a solid support that is attached to an unlabeled component, whereby the label is recruited to the solid support by virtue of forming a stabilized ternary complex. As such, the support-attached component can be detected or identified based on observation of the recruited label. Whether used in solution phase or on a solid support, exogenous labels can be useful for detecting a stabilized ternary complex or an individual component thereof, during an examination step. An exogenous label can remain attached to a component after the component dissociates from other components that had formed a stabilized ternary complex. Exemplary labels, methods for attaching labels and methods for using labeled components are set forth in commonly owned U.S. Pat. App. Pub. No. 2017/0022553 A1 or U.S. patent application Ser. No. 15/677,870, published as U.S. Pat. App. Pub. No. 2018/0044727 A1; Ser. No. 15/851,383, published as U.S. Pat. App. Pub. No. 2018/0187245 A1; Ser. No. 15/873,343, published as U.S. Pat. App. Pub. No. 2018/0208983 A1; 62/450,397 or 62/506,759, each of which is incorporated herein by reference.

Examples of useful exogenous labels include, but are not limited to, radiolabel moieties, luminophore moieties, fluorophore moieties, quantum dot moieties, chromophore moieties, enzyme moieties, electromagnetic spin labeled moieties, nanoparticle light scattering moieties, and any of a variety of other signal generating moieties known in the art. Suitable enzyme moieties include, for example, horseradish peroxidase, alkaline phosphatase, beta-galactosidase, or acetylcholinesterase. Exemplary fluorophore moieties include, but are not limited to umbelliferone, fluorescein, isothiocyanate, rhodamine, tetramethyl rhodamine, eosin, green fluorescent protein and wavelength shifted variants thereof, erythrosin, coumarin, methyl coumarin, pyrene, malachite green, stilbene, Lucifer Yellow™, Cascade Blue™, Texas Red™, DyLight® dyes, CF® yes, dansyl chloride, phycoerythrin, phycocyanin, fluorescent lanthanide complexes such as those including Europium and Terbium, Cy3, Cy5, Cy7, Alexa Fluor® dyes and others known in the art such as those described in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland.

A secondary label can be used in a method of the present disclosure. A secondary label is a binding moiety that can bind specifically to a partner moiety. For example, a ligand moiety can be attached to a polymerase, nucleic acid or nucleotide to allow detection via specific affinity of the ligand for a labeled receptor. Exemplary pairs of binding moieties that can be used include, without limitation, antigen and immunoglobulin or active fragments thereof, such as FAbs; immunoglobulin and immunoglobulin (or active fragments, respectively); avidin and biotin, or analogs thereof having specificity for avidin; streptavidin and biotin, or analogs thereof having specificity for streptavidin; complementary oligonucleotides; or carbohydrates and lectins.

In some embodiments, the secondary label can be a chemically modifiable moiety. In this embodiment, labels having reactive functional groups can be incorporated into a stabilized ternary complex. Subsequently, the functional group can be covalently reacted with a primary label moiety. Suitable functional groups include, but are not limited to, amino groups, carboxy groups, maleimide groups, oxo groups and thiol groups.

In alternative embodiments, a ternary complex can lack exogenous labels. For example, a ternary complex and all components participating in the ternary complex (e.g. polymerase, template nucleic acid, primer and/or cognate nucleotide) can lack one, several or all of the exogenous labels described herein or in the above-incorporated references. In such embodiments, ternary complexes can be detected based on intrinsic properties of the stabilized ternary complex, such as mass, charge, intrinsic optical properties or the like. Exemplary methods for detecting non-labeled ternary complexes are set forth in commonly owned U.S. Pat. App. Pub. No. 2017/0022553 A1 PCT App. Ser. No. PCT/US16/68916, published as WO 2017/117243, or U.S. Pat. App. Ser. No. 62/375,379 or Ser. No. 15/677,870, published as US Pat. App. Pub. No. 2018/0044727 A1, each of which is incorporated herein by reference.

Generally, detection can be achieved in an examination step by methods that perceive a property that is intrinsic to a ternary complex or a label moiety attached thereto. Exemplary properties upon which detection can be based include, but are not limited to, mass, electrical conductivity, energy absorbance, luminescence or the like. Detection of luminescence can be carried out using methods known in the art pertaining to nucleic acid arrays. A luminophore can be detected based on any of a variety of luminescence properties including, for example, emission wavelength, excitation wavelength, fluorescence resonance energy transfer (FRET) intensity, quenching, anisotropy or lifetime. Other detection techniques that can be used in a method set forth herein include, for example, mass spectrometry which can be used to perceive mass; surface plasmon resonance which can be used to perceive binding at a surface; absorbance which can be used to perceive the wavelength of the energy a label absorbs; calorimetry which can be used to perceive changes in temperature due to presence of a label; electrical conductance or impedance which can be used to perceive electrical properties of a label, or other known analytic techniques. Examples of reagents and conditions that can be used to create, manipulate and detect stabilized ternary complexes include, for example, those set forth in commonly owned U.S. Pat. App. Pub. No. 2017/0022553 A1; PCT App. Ser. No. PCT/US16/68916; or U.S. patent application Ser. No. 15/677,870, published as U.S. Pat. App. Pub. No. 2018/0044727 A1; Ser. No. 15/851,383, published as U.S. Pat. App. Pub. No. 2018/0187245 A1; Ser. No. 15/873,343, published as U.S. Pat. App. Pub. No. 2018/0208983 A; 62/450,397 or 62/506,759, each of which is incorporated herein by reference.

Some embodiments of the methods set forth herein utilize two or more distinguishable signals to distinguish stabilized ternary complexes from each other and/or to distinguish one base type in a template nucleic acid from another base type. For example, two or more luminophores can be distinguished from each other based on unique optical properties such as unique wavelength for excitation or unique wavelength of emission. In particular embodiments, a method can distinguish different stabilized ternary complexes based on differences in luminescence intensity. For example, a first ternary complex can be detected in a condition where it emits less intensity than a second ternary complex. Such intensity scaling (sometimes called 'grey scaling') can exploit any distinguishable intensity difference. Exemplary differences include a particular stabilized ternary complex having an intensity that is at most 10%, 25%, 33%, 50%, 66%, or 75% compared to the intensity of another stabilized ternary complex that is to be detected.

Intensity differences can result from using different luminophores, for example, each having a different extinction coefficient (i.e. resulting in different excitation properties) and/or different luminescence quantum yield (i.e. resulting in different emission properties). Alternatively, the same luminophore type can be used but can be present in different amounts. For example, all members of a first population of ternary complexes can be labeled with a particular luminophore, whereas a second population has only half of its members labeled with the luminophore. In this example, the second population would be expected to produce half the signal of the first population. The second population can be produced, for example, by using a mixture of labeled nucleotides and unlabeled nucleotides (in contrast to the first population containing primarily labeled nucleotides). Similarly, the second population can be produced, for example, by using a mixture of labeled polymerases and unlabeled polymerases (in contrast to the first population containing primarily labeled polymerases). In an alternative labeling scheme, a first population of ternary complexes can include polymerase molecules that have multiple labels that produce a particular luminescent signal and a second population of ternary complexes can include polymerase molecules that each have only one of the labels that produces the luminescent signal.

In some embodiments, the examination step is carried out in a way that the identity of at least one nucleotide type is imputed, for example, as set forth in commonly owned U.S. Pat. No. 9,951,385 or U.S. patent application Ser. No. 15/922,787, granted as U.S. Pat. No. 10,161,003, each of which is incorporated herein by reference. Alternatively or additionally to using imputation, an examination step can use disambiguation to identify one or more nucleotide types, for example, as set forth in commonly owned U.S. Pat. No. 9,951,385 or U.S. patent application Ser. No. 15/922,787, granted as U.S. Pat. No. 10,161,003, each of which is incorporated herein by reference.

A method of the present disclosure can be performed in a mode whereby different nucleotide types are serially delivered and then removed from a vessel where ternary complex is to be formed and examined. In this mode, a first nucleotide type can be delivered to a reaction vessel and then removed from the vessel prior to delivering a second nucleotide type to the vessel. Polymerase can be retained in the vessel when the nucleotide is removed. As such, polymerase can be delivered to a flow cell initially to create conditions that facilitate ternary complex formation with the first nucleotide and new polymerase can be, but need not be, added in a subsequent delivery to facilitate ternary complex formation with nucleotides that are subsequently delivered.

Accordingly, a method for identifying a nucleotide in a primed template nucleic acid can include steps of (a) providing a vessel having a primed template nucleic acid, polymerase and a nucleotide cognate of a first base type; (b) examining the vessel for a stabilized ternary complex including the polymerase and the nucleotide cognate of the first base type bound at a base position of the primed template nucleic acid; (c) removing the nucleotide cognate of the first base type from the vessel and delivering a nucleotide cognate of a second base type to the vessel, whereby the vessel retains the primed template nucleic acid and the polymerase from step (b); (d) examining the vessel for a stabilized ternary complex including the polymerase and the nucleotide cognate of the second base type bound at the base position of the primed template nucleic acid; and (e) identifying the type of nucleotide at the base position of the primed template nucleic acid.

Furthermore, a method for identifying a nucleotide in a primed template nucleic acid can include steps of (a) providing an array of primed template nucleic acids; (b) forming stabilized ternary complexes each including a polymerase, a nucleotide cognate of a first base type and a primed template nucleic acid in the array; (c) detecting the stabilized ternary complexes in the array; (d) removing the nucleotide cognate of the first base type from the array and then repeating steps (b) and (c) for a nucleotide cognate of a second base type, whereby the primed template nucleic acids and the polymerases are retained in the array; and (e) identifying the type of nucleotide that is present in each of the stabilized ternary complexes detected in step (c).

Further still, a method for identifying a nucleotide in a primed template nucleic acid, that includes steps of (a) providing an array of primed template nucleic acids; (b) delivering a plurality of polymerases and a plurality of nucleotide cognates of a first base type to the array, thereby forming stabilized ternary complexes each including a polymerase of the plurality of polymerases, a nucleotide of the plurality of nucleotide cognates of the first base type and a primed template nucleic acid of the array; (c) detecting the stabilized ternary complexes in the array; (d) removing the nucleotide cognate of the first base type from the array and then repeating steps (b) and (c) for nucleotide cognates of a second base type, whereby primed template nucleic acids of the array and polymerases of the plurality of polymerases are retained in the array; and (e) identifying the type of nucleotide that is present in each of the stabilized ternary complexes detected in step (c).

A nucleotide cognate can be removed from a vessel under conditions that will dissociate the nucleotide from a ternary complex, thereby allowing the nucleotide to be separated from the primed template nucleic acid without causing substantial removal of the polymerase. For example, the dissociated nucleotide can be removed via flow of fluid away from the primed template nucleic acid, decanting fluid away from the primed template nucleic acid, separating a solid support that is attached to the primed template nucleic acid from the fluid, etc. Another nucleotide (typically, but not always, a different type of nucleotide from the one that was previously removed) can then be delivered to the primed template nucleic acid. Delivery of more polymerase is not necessary if the polymerase is not substantially removed from the presence of the primed template nucleic acid. This provides a savings of time and resources that would otherwise be spent preparing more polymerase.

Any of a variety of techniques can be used to remove a nucleotide from a ternary complex, without substantially removing the primed template nucleic acid and polymerase. For example, the primed template nucleic acid and the polymerase can both be immobilized on a solid support such that disruption of the equilibrium conditions under which the ternary complex formed will result in dissociation of the nucleotide into solution and away from the immobilized components. Separation of the fluid from the immobilized components will result in separation of the nucleotide from the primed template nucleic acid and polymerase. Merely reducing the concentration of unbound nucleotide in the fluid (e.g. by removing unbound nucleotide from the fluid surrounding the polymerase and primed template nucleic acid) will cause dissociation via the shift in binding equilibrium. As an alternative or addition to reducing the nucleotide concentration, a nucleotide can be dissociated from a ternary complex using chemical or physical conditions that disrupt the non-covalent forces that bind the components of the ternary complex. Exemplary conditions are set forth in further detail below.

Linkers that are relatively long and flexible are particularly useful when immobilizing two components that are capable of participating in a ternary complex. The length and flexibility will allow the two components to associate and dissociate from each other while being localized on a solid support. Exemplary linkers include, but are not limited to, those that include polyethylene glycol (PEG), nucleic acid, peptide nucleic acids, peptides, polypropylene glycol, polyethylene, polypropylene, polyamides, polyesters and the like, Exemplary linkers and reactive groups for their attachment are set forth in Krishnamurthy et al., (2007) *J. Am. Chem. Soc.*, 129:1312-1320 and US Pat. App. Pub. No. 2016/0032379 A1, each of which is incorporated herein by reference.

In another exemplary embodiment, only one of the components of the ternary complex is immobilized. For example, the primed template nucleic acid or the polymerase can be immobilized on a solid support. Immobilization can be mediated by a linker such as those set forth above or by chemistries that are used to attach analytes to arrays as set forth herein or in references cited in connection with arrays herein. In such embodiments, the ternary complex can be dissociated using chemical or physical conditions that selectively dissociate the nucleotide from the polymerase and primed template nucleic acid while maintaining association between the polymerase and primed template nucleic acid. This association can be exploited to maintain the polymerase and primed template nucleic acid so long as one of the pair is immobilized to a solid support. The nucleotide can then be removed by separating the fluid containing nucleotide from the solid support. A single component of a ternary complex can be immobilized using a linker set forth above in the context of immobilizing two components. Other immobilization moieties can also be used whether or not they have the flexibility or length of the above-exemplified linkers.

Physical conditions that can be used to dissociate nucleotide from a ternary complex in a method set forth herein include, for example, temperature elevated to a range above physiological range, thereby causing selective dissociation of a nucleotide from a ternary complex or electrical current that attracts charged nucleotide species away from polymerase and nucleic acid. Nucleotides having physically manipulable moieties such as chromophores that are responsive to optical tweezers or optical trapping, a ferromagnet or magnet that is responsive to magnetic manipulation, or double bonds that can be photo-isomerized from a high affinity binding state to a low affinity binding state (or vice versa) In particular embodiments, the physical conditions are selected to maintain the binding of polymerase to the nucleic acid while dissociating the nucleotide from the polymerase and nucleic acid.

Chemical conditions that can be used to dissociate nucleotide from a ternary complex include, for example, high salt. Useful high salt conditions include, for example, at least 50 mM, 100 mM, 150 mM, 200 mM, 300 mM, 400 mM, 500 mM or higher concentrations of salt. Alternatively or additionally, the salt concentration can be at most 500 mM, 400 mM, 300 mM, 200 mM, 150 mM, 100 mM, 50 mM or lower concentration. Useful salts include, but are not limited to KCl, NaCl, guanidinium thiocyanate and other salts used for biochemical reactions.

Another useful chemical condition for dissociating a nucleotide from a ternary complex is the presence of organic solvents in an amount that is at least 10%, 20%, 30%, 40%, 50% or more organic solvent in an aqueous solution (v/v). Alternatively or additionally, organic solvent can be present in an amount that is no more than 50%, 40%, 30%, 20%, 10% or less organic solvent in aqueous solution (v/v). Particularly useful organic solvents are alcohols which can optionally be present in an amount that is at least 10%, 20%, 30%, 40%, 50% or more alcohol in an aqueous solution (v/v). Alternatively or additionally, alcohol can be present in an amount that is no more than 50%, 40%, 30%, 20%, 10% or less alcohol in an aqueous solution (v/v). Ethanol, methanol, isopropanol, diol, and 1,3 butanediol are particularly useful alcohols. Other polar solvents, such as polar protic organic solvents (e.g. buffered organic acids) and polar aprotic organic solvents (e.g. DMSO, DMF), can also be used. Generally, the organic solvent (e.g. alcohol) is miscible in aqueous solution or present in an amount that is soluble in aqueous solution. In particular embodiments, salt and organic solvent (e.g. alcohol) are both present, for example, each in an amount set forth above.

A further useful chemical condition for dissociating a nucleotide from a ternary complex is pH outside of the physiological range (e.g. at or below pH 6, 5, or 4; at or above pH 8, 9 or 10). Other reagents that can be useful include, but are not limited to, redox reagents such as dithiothreitol, glutathione or 2-mercaptoethanol; detergents such as anionic, cationic or zwitterionic detergents; or proteins that bind to nucleotides (e.g. proteins that compete with polymerase for binding to nucleotides). The chemical conditions set forth herein for dissociating nucleotide from a ternary complex can be used in various combinations (e.g. an aqueous solution can have a pH outside of physiological range and can also include a miscible organic solvent). As a further option, one or more chemical condition for dissociating nucleotide from a ternary complex can be combined with a physical condition for dissociating nucleotide from a ternary complex.

When performing the methods in a mode whereby different nucleotide types are serially delivered to a reaction vessel and then removed from the vessel, examination of the vessel for ternary complexes can be carried out after each delivery. In this mode, ternary complexes of different types (i.e. ternary complexes that differ in the type of nucleotide that is present) will form after each delivery. Ternary complexes that had formed in previous deliveries of other types of nucleotides will have dissociated since the other types of nucleotides had been removed. As such, ternary complexes formed from each type of nucleotide can be identified based on the expectation that one type of ternary complex will be most prominent in each examination. For example, when ternary complex is detected based on recruitment of a labeled polymerase or labeled nucleotide to primed template nucleic acids in an array, the array features having the highest signal can be identified as the features where ternary complex has formed. The type of ternary complex (i.e. the type of nucleotide present in the ternary complex) that forms at each of the features can be deduced from knowledge of which nucleotide was delivered prior to the examination step.

In this mode, the different types of ternary complexes need not be distinguished by unique labels. Rather, the different types of ternary complexes can be distinguished based on temporal information pertaining to when they formed and which nucleotide type was delivered to induce formation. If desired, the different types of ternary complexes can be distinguishably labeled. For example, each nucleotide type can have a label that produces a signal that is distinguished from all other nucleotide types used. Distinguishable labels can provide the advantage of increasing the speed of detection since a single examination step can be carried out after multiple different types of nucleotides have been delivered. Time savings can be achieved by simultaneously delivering two or more distinguishably labeled nucleotide types in a method set forth herein. If desired, examination can occur after each nucleotide delivery even when using distinguishable labels to identify different types of ternary complexes.

A method of the present disclosure can be performed in a mode whereby different nucleotide types are serially delivered to a vessel where ternary complex is to be formed and examined. In this mode, a first nucleotide type can be delivered to a reaction vessel and then a second nucleotide type can be delivered to the vessel such that the two nucleotide types accumulate in the vessel. When the vessel contains a variety of different primed template nucleic acids, for example an array or other multiplex format, multiple different types of ternary complexes can accumulate in the vessel. Polymerase can be added initially to create conditions that facilitate ternary complex formation with the first nucleotide. New polymerase can be, but need not be, added in a subsequent delivery to facilitate ternary complex formation with a subsequently delivered nucleotide.

Accordingly, a method for identifying a nucleotide in a primed template nucleic acid can include steps of (a) providing a vessel having a primed template nucleic acid, polymerase and a nucleotide cognate of a first base type; (b) examining the vessel for a stabilized ternary complex including the polymerase and the nucleotide cognate of the first base type bound at a base position of the primed template nucleic acid; (c) delivering a nucleotide cognate of a second base type to the vessel, whereby the vessel retains the nucleotide cognate of the first base type, the primed template nucleic acid and the polymerase from step (b); (d) examining the vessel for a stabilized ternary complex including the polymerase and the nucleotide cognate of the second base type bound at the base position of the primed template nucleic acid; and (e) identifying the type of nucleotide at the base position of the primed template nucleic acid.

A method for identifying a nucleotide in a primed template nucleic acid can also include steps of (a) providing an array of primed template nucleic acids; (b) forming stabilized ternary complexes each including a polymerase, a nucleotide cognate of a first base type and a primed template nucleic acid in the array; (c) detecting the stabilized ternary complexes in the array; (d) repeating steps (b) and (c) for a nucleotide cognate of a second base type, whereby the primed template nucleic acids, the nucleotide cognate of the first base type and the polymerases are retained in the array; and (e) identifying the type of nucleotide that is present in each of the stabilized ternary complexes detected in step (c).

A method for identifying a nucleotide in a primed template nucleic acid can optionally include steps of (a) providing an array of primed template nucleic acids; (b) delivering a plurality of polymerases and a plurality of nucleotide cognates of a first base type to the array, thereby forming stabilized ternary complexes each including a polymerase of the plurality of polymerases, a nucleotide of the plurality of nucleotide cognates of the first base type and a primed template nucleic acid of the array; (c) detecting the stabilized ternary complexes in the array; (d) repeating steps (b) and (c) for nucleotide cognates of a second base type, whereby primed template nucleic acids of the array, nucleotides of the plurality of nucleotides and polymerases of the plurality of polymerases are retained in the array; and (e) identifying the type of nucleotide that is present in each of the stabilized ternary complexes detected in step (c).

When performing the methods in a mode whereby different nucleotide types are serially delivered to a reaction vessel such that the different nucleotides accumulate, examination of the vessel for ternary complexes can be carried out after each delivery. In this mode, ternary complexes of different types (i.e. ternary complexes that differ in the type of nucleotide that is present) will form after each delivery. Ternary complexes that had formed in previous deliveries of other types of nucleotides will also be present in the vessel. As such, ternary complexes formed from each type of nucleotide can be identified based on the appearance of newly formed ternary complex from one examination to the next. For example, when ternary complex is detected based on recruitment of a labeled polymerase or labeled nucleotide to primed template nucleic acids in an array, the array features having increased signal intensity compared to the signal intensity detected for that feature in previous examinations can be identified as the features where new ternary complex has formed. The type of ternary complex (i.e. the type of nucleotide present in the ternary complex) that forms at each of the features can be deduced from knowledge of which nucleotide was delivered prior to the examination step where new ternary complex signal arose.

Thus, the different types of ternary complexes need not be distinguished by unique labels. Rather, the different types of ternary complexes can be distinguished based on temporal information pertaining to when they formed and which nucleotide type was delivered to induce formation of the ternary complex. If desired, the different types of ternary complexes can be distinguishably labeled. For example, two or more nucleotide types can have labels that produce signals that are distinguished from each other. In some embodiments, all nucleotide types can be distinguished based on unique labels. Thus, labels can distinguish nucleotides that pair with one type of nucleotide in a template from nucleotides that pair with all other nucleotide types in the template. Distinguishable labels can provide the advantage of increasing the speed of detection since a single examination step can be carried out after all nucleotides have been serially delivered. If desired, examination can occur after each nucleotide delivery even when using distinguishable labels to identify different types of ternary complexes.

Multiple nucleotide delivery and examination steps can be carried out at a given position in a primed template nucleic acid. In a sequencing embodiment, multiple examination steps can be carried out in a subroutine that is carried out during a single sequencing cycle prior to extending the primer to move to the next sequencing cycle.

Accordingly, the present disclosure provides a method for identifying a nucleotide in a primed template nucleic acid. The method can include steps of (a) providing a vessel having a primed template nucleic acid, polymerase and a nucleotide cognate of a first base type; (b) examining the vessel for a stabilized ternary complex including the polymerase and the nucleotide cognate of the first base type bound at a base position of the primed template nucleic acid; (c) delivering a nucleotide cognate of a second base type to the vessel, whereby the vessel retains the primed template nucleic acid and the polymerase from step (b); (d) examining the vessel for a stabilized ternary complex including the polymerase and the nucleotide cognate of the second base type bound at the base position of the primed template nucleic acid; (e) identifying the type of nucleotide at the base position of the primed template nucleic acid; (f) delivering a nucleotide cognate of a third base type to the vessel, whereby the vessel retains the primed template nucleic acid and the polymerase from step (b); and (g) examining the vessel for a stabilized ternary complex including the polymerase and the nucleotide cognate of the third base type bound at the base position of the primed template nucleic acid. Optionally, the method further includes steps of (h)

delivering a nucleotide cognate of a fourth base type to the vessel, whereby the vessel retains the primed template nucleic acid and the polymerase from step (b); and (i) examining the vessel for a stabilized ternary complex including the polymerase and the nucleotide cognate of the fourth base type bound at the base position of the primed template nucleic acid.

Also provided is a method for identifying a nucleotide in a primed template nucleic acid, that includes steps of (a) providing an array of primed template nucleic acids; (b) forming stabilized ternary complexes each including a polymerase, a nucleotide cognate of a first base type and a primed template nucleic acid in the array; (c) detecting the stabilized ternary complexes in the array; (d) repeating steps (b) and (c) for a nucleotide cognate of a second base type, whereby the primed template nucleic acids and the polymerases are retained in the array; and (e) identifying the type of nucleotide that is present in each of the stabilized ternary complexes detected in step (c). Optionally, step (d) is carried out by repeating steps (b) and (c) for the nucleotide cognate of the second base type, and then repeating steps (b) and (c) for a nucleotide cognate of a third base type. Further optionally, step (d) is carried out by repeating steps (b) and (c) for the nucleotide cognate of the second base type, then repeating steps (b) and (c) for the nucleotide cognate of the third base type and then repeating steps (b) and (c) for a nucleotide cognate of a fourth base type.

Also provided is a method for identifying a nucleotide in a primed template nucleic acid, that includes steps of (a) providing an array of primed template nucleic acids; (b) delivering a plurality of polymerases and a plurality of nucleotide cognates of a first base type to the array, thereby forming stabilized ternary complexes each including a polymerase of the plurality of polymerases, a nucleotide of the plurality of nucleotide cognates of the first base type and a primed template nucleic acid of the array; (c) detecting the stabilized ternary complexes in the array; (d) repeating steps (b) and (c) for nucleotide cognates of a second base type, whereby primed template nucleic acids of the array and polymerases of the plurality of polymerases are retained in the array; and (e) identifying the type of nucleotide that is present in each of the stabilized ternary complexes detected in step (c). Optionally, step (d) is carried out by repeating steps (b) and (c) for the nucleotide cognates of the second base type, and then repeating steps (b) and (c) for nucleotide cognates of a third base type. Further optionally, step (d) is carried out by repeating steps (b) and (c) for the nucleotide cognates of the second base type, then repeating steps (b) and (c) for the nucleotide cognates of the third base type and then repeating steps (b) and (c) for nucleotide cognates of a fourth base type.

For ease of explanation, methods of the present disclosure are exemplified herein with respect to stabilized ternary complex(es) formed in the presence of nucleotide cognate for one base type. It will be understood, that ternary complex (es) can be formed in the presence of nucleotide cognate(s) for only one base type, for example, in the presence of only a single type of nucleotide or in the presence of one or more nucleotide types that are cognates for the same base type. Alternatively, ternary complex(es) can be formed in the presence of a mixture of nucleotide types that are cognates for more than one base type expected to be in a template nucleic acid. For example, the nucleotide types that are present in a particular step of the methods set forth herein can be cognates for at least 2, 3 or 4 different base types expected to be in a template nucleic acid. Alternatively or additionally, the nucleotide types that are present in a particular step of the methods set forth herein can be cognates for at most 4, 3 or 2 different base types. The different nucleotide types can be mixed with each other prior to being delivered to a vessel where a primed template nucleic acid occurs. In other embodiments, different nucleotide types can be serially delivered to a vessel where a primed template nucleic acid occurs. As such, the different nucleotides will accumulate to create a reaction mixture where the different types of nucleotides are simultaneously present with the primed template nucleic acid.

Accordingly, the present disclosure provides a method for identifying a nucleotide in a primed template nucleic acid that includes steps of (a) providing a vessel having a primed template nucleic acid, polymerase, a nucleotide cognate of a first base type and a nucleotide cognate of a third base type; (b) examining the vessel for a stabilized ternary complex including the polymerase and (i) the nucleotide cognate of the first base type bound at the base position of the primed template nucleic acid or (ii) the nucleotide cognate of the third base type bound at the base position of the primed template nucleic acid; (c) delivering a nucleotide cognate of a second base type to the vessel, whereby the vessel retains the primed template nucleic acid and the polymerase from step (b); (d) examining the vessel for a stabilized ternary complex including the polymerase and the nucleotide cognate of the second base type bound at the base position of the primed template nucleic acid; and (e) identifying the type of nucleotide at the base position of the primed template nucleic acid. Optionally, step (c) further includes delivering a nucleotide cognate of a fourth base type to the vessel, and step (d) includes examining the vessel for a stabilized ternary complex including the polymerase and (i) the nucleotide cognate of the second base type bound at the base position of the primed template nucleic acid or (ii) the nucleotide cognate of the fourth base type bound at the base position of the primed template nucleic acid.

Furthermore, the present disclosure provides a method for identifying a nucleotide in a primed template nucleic acid that includes steps of (a) providing an array of primed template nucleic acids; (b) forming stabilized ternary complexes including a polymerase, a primed template nucleic acid in the array and a nucleotide cognate of a first base type and forming stabilized ternary complexes including a polymerase, a primed template nucleic acid in the array and a nucleotide cognate of a third base type; (c) detecting the stabilized ternary complexes in the array that include the nucleotide cognates of the first base type and third base type; (d) repeating steps (b) and (c) for a nucleotide cognate of a second base type, whereby the primed template nucleic acids and the polymerases are retained in the array; and (e) identifying the type of nucleotide that is present in each of the stabilized ternary complexes detected in step (c).

Also provided is a method for identifying a nucleotide in a primed template nucleic acid, that includes steps of (a) providing an array of primed template nucleic acids; (b) delivering a plurality of polymerases, a plurality of nucleotide cognates of a first base type, and a plurality of nucleotide cognates of a third base type to the array, thereby forming stabilized ternary complexes including a polymerase of the plurality of polymerases, a primed template nucleic acid of the array, and a nucleotide of the plurality of nucleotide cognates of the first base type or the third base type; (c) detecting the stabilized ternary complexes in the array; (d) repeating steps (b) and (c) for nucleotide cognates of a second base type, whereby primed template nucleic acids of the array and polymerases of the plurality of polymerases are retained in the array; and (e) identifying the type of nucleotide that is present in each of the stabilized ternary complexes detected in step (c).

A method of the present disclosure can include a step of modifying a primer, for example, to extend the primer by addition of one or more nucleotides. In particular embodiments, a nucleotide that is added to a primer will include a reversible terminator moiety. The reversible terminator moiety can provide the non-limiting benefits of preventing more than one nucleotide from being added to the primer during the extension process and stabilizing ternary complex formation at the 3' end of the primer during an examination process.

Typically, a nucleotide, such as a reversibly terminated nucleotide, that is added to a primer in a method set forth herein does not have an exogenous label. This is because the extended primer need not be detected in a method set forth herein. However, if desired, one or more types of reversibly terminated nucleotides used in a method set forth herein can be detected, for example, via exogenous labels attached to the nucleotides.

A primer extension process or a process of forming a ternary complex need not use a labeled polymerase. For example, a polymerase that is used for an extension step need not be attached to an exogenous label (e.g. covalently or otherwise). Alternatively, a polymerase that is used for primer extension can include an exogenous label, for example, a label that was used in a previous examination step.

Examples of reagents and conditions that can be used for a polymerase-based primer extension step include, for example, those set forth in commonly owned U.S. Pat. App. Pub. No. 2017/0022553 A1 or U.S. patent application Ser. No. 15/677,870, published as U.S. Pat. App. Pub. No. 2018/0044727 A1; Ser. No. 15/851,383, published as U.S. Pat. App. Pub. No. 2018/0187245 A1; 62/450,397 or 62/506,759, each of which is incorporated herein by reference. Exemplary reversible terminator moieties, methods for incorporating them into primers and methods for modifying the primers for further extension (often referred to as 'deblocking') are set forth in U.S. Pat. Nos. 7,544,794; 7,956,171; 8,034,923; 8,071,755; 8,808,989; or 9,399,798. Further examples are set forth in Bentley et al., *Nature* 456:53-59 (2008), WO 04/018497; U.S. Pat. No. 7,057,026; WO 91/06678; WO 07/123744; U.S. Pat. Nos. 7,329,492, 7,211,414; 7,315,019; 7,405,281, and US 2008/0108082, each of which is incorporated herein by reference.

In particular embodiments, reagents that are used during a primer extension process are removed from contact with the primed template nucleic acid prior to a step of forming a stabilized ternary complex with the primer-template hybrid. For example, removal of a nucleotide mixture that was used for an extension step can be desirable when one or more types of nucleotides in the mixture would interfere with formation or detection of a ternary complex in a subsequent examination step. Similarly, it may be desirable to remove polymerases or cofactors that were used in a primer modification step so as to prevent unwanted catalytic activity during a subsequent examination step. Removal can be followed by a wash step, wherein an inert fluid is used to purge the primer-template hybrid of residual components of the reagent mixture used for primer modification.

A reagent removal or wash procedure can be performed between any of a variety of steps set forth herein. Such procedures can be used to remove one or more of the reagents that are present in a reaction vessel or on a solid support. For example, a reagent removal or wash step can be useful for separating a primer-template hybrid from other reagents that were contacted with the primer-template hybrid under ternary complex stabilizing conditions. In particular embodiments, separation of reagents is facilitated by attachment of a reagent of interest, such as a primed template nucleic acid, to a solid support and removal of fluid from contact with the solid support. One or more of the reagents set forth herein can be attached to a solid support or provided in solution as desired to suit a particular use of the methods or apparatus set forth herein.

A reagent removal or wash procedure can be used to remove one or more reagents from interfering with examination of a ternary complex or from contaminating a second ternary complex that is to be formed on a substrate (or in a vessel) that had previously been in contact with reagents used to form the first ternary complex. For example, a primed template nucleic acid can be contacted with a polymerase and at least one nucleotide type to form a first mixture under ternary complex stabilizing conditions, and the first mixture, or a product thereof, can be examined. However, reagent removal and washing need not be carried out between steps or processes set forth herein. For example, it may be desirable to avoid removing one or more reagents between examination steps. As set forth in further detail elsewhere herein, when different ternary complex species are formed serially, a polymerase or nucleotide that was used to form a first ternary complex species need not be removed nor washed away when a second ternary complex species is formed.

Optionally, a wash can be carried out prior to detection in order to remove reagents that are not participating in formation of a stabilized ternary complex. Alternatively or additionally, a wash can be carried out after the detection step to remove one or more component of the first mixture from the primer-template hybrid. Then the primed template nucleic acid can be contacted with a polymerase and at least one other nucleotide to form a second mixture under ternary complex stabilizing conditions, and the second mixture can be examined for ternary complex formation. As before, an optional wash can be carried out prior to the second examination to remove reagents that are not participating in formation of a stabilized ternary complex.

Nucleotides present in an examination step may cause unwanted side reactions, such as nucleotide incorporation reactions, if carried over into a primer extension process. Thus, a reagent removal or wash step can be employed prior to a primer extension step. Optionally, free nucleotides or other examination reagents may be modified or disabled, for example, by enzymes such as phosphatases, by chemical modification or by physical techniques.

The present disclosure provides a method for sequencing a primed template nucleic acid. The method can include steps of (a) providing a vessel having a primed template nucleic acid, first polymerase and a nucleotide cognate of a first base type; (b) examining the vessel for a stabilized ternary complex including the first polymerase and the nucleotide cognate of the first base type bound at a base position of the primed template nucleic acid; (c) delivering a nucleotide cognate of a second base type to the vessel, whereby the vessel retains the primed template nucleic acid and the first polymerase from step (b); (d) examining the vessel for a stabilized ternary complex including the first polymerase and the nucleotide cognate of the second base type bound at the base position of the primed template nucleic acid; (e) identifying the type of nucleotide at the base position of the primed template nucleic acid; (f) delivering a nucleotide cognate of a third base type to the vessel, whereby the vessel retains the primed template nucleic acid and the first polymerase from step (b); (g) examining the vessel for a stabilized ternary complex including the first polymerase and the nucleotide cognate of the third base type bound at the base position of the primed template nucleic acid; (h) delivering a nucleotide cognate of a fourth base type to the vessel, whereby the vessel retains the primed template nucleic acid and the first polymerase from step (b); (i) examining the vessel for a stabilized ternary complex including the first polymerase and the nucleotide cognate of the fourth base type bound at the base position of the primed template nucleic acid; (j) adding a nucleotide to the primer of the primed template nucleic acid, whereby the vessel comprises an extended primed template nucleic acid; (k) delivering a second polymerase and a nucleotide cognate of the first base type to the vessel; and (l) repeating steps (b) through (i) using the extended primed template instead of the primed template nucleic acid and using the second polymerase instead of the first polymerase. The first polymerase may be the same type of polymerase as the first type, or the first and second polymerase may be different types of polymerase.

Further provided is a method for sequencing a primed template nucleic acid that includes steps of (a) providing a vessel having a primed template nucleic acid, first polymerase and a nucleotide cognate of a first base type; (b) examining the vessel for a stabilized ternary complex including the first polymerase and the nucleotide cognate of the first base type bound at a base position of the primed template nucleic acid; (c) delivering a nucleotide cognate of a second base type to the vessel, whereby the vessel retains the primed template nucleic acid and the first polymerase from step (b); (d) examining the vessel for a stabilized ternary complex including the first polymerase and the nucleotide cognate of the second base type bound at the base position of the primed template nucleic acid; (e) identifying the type of nucleotide at the base position of the primed template nucleic acid; (f) adding a nucleotide to the primer of the primed template nucleic acid, whereby the vessel includes an extended primed template nucleic acid; (g) delivering a second polymerase and a nucleotide cognate of the first base type to the vessel; and (h) repeating steps (b) through (e) using the extended primed template instead of the primed template nucleic acid and using the second polymerase instead of the first polymerase. The first polymerase may be the same type of polymerase as the first type, or the first and second polymerase may be different types of polymerase.

Also provided is a method for sequencing primed template nucleic acids, that includes steps of (a) providing an array of primed template nucleic acids; (b) forming stabilized ternary complexes each including a first polymerase, a nucleotide cognate of a first base type and a primed template nucleic acid in the array; (c) detecting the stabilized ternary complexes in the array; (d) repeating steps (b) and (c) for a nucleotide cognate of a second base type, then repeating steps (b) and (c) for the nucleotide cognate of the third base type and then repeating steps (b) and (c) for a nucleotide cognate of a fourth base type, whereby the primed template nucleic acids and the first polymerases are retained in the array; (e) identifying the type of nucleotide that is present in each of the stabilized ternary complexes detected in step (c); (f) adding a nucleotide to the primer of each of the primed template nucleic acids, whereby the array includes extended primed template nucleic acids; and (g) repeating steps (b) through (e) using the extended primed template instead of the primed template nucleic acid and using a second polymerase instead of the first polymerase. The first polymerase may be the same type of polymerase as the first type, or the first and second polymerase may be different types of polymerase.

A method for sequencing a primed template nucleic acids can include steps of (a) providing an array of primed template nucleic acids; (b) forming stabilized ternary complexes each including a first polymerase, a nucleotide cognate of a first base type and a primed template nucleic acid in the array; (c) detecting the stabilized ternary complexes in the array; (d) repeating steps (b) and (c) for a nucleotide cognate of a second base type, whereby the primed template nucleic acids and the first polymerases are retained in the array; (e) identifying the type of nucleotide that is present in each of the stabilized ternary complexes detected in step (c); (f) adding a nucleotide to the primer of each of the primed template nucleic acids, whereby the array includes extended primed template nucleic acids; and (g) repeating steps (b) through (e) using the extended primed template instead of the primed template nucleic acid and using a second polymerase instead of the first polymerase. The first polymerase may be the same type of polymerase as the first type, or the first and second polymerase may be different types of polymerase.

Also provided is a method for sequencing primed template nucleic acids, that includes steps of (a) providing an array of primed template nucleic acids; (b) delivering a plurality of polymerases and a plurality of nucleotide cognates of a first base type to the array, thereby forming stabilized ternary complexes each including a polymerase of the plurality of polymerases, a nucleotide of the plurality of nucleotide cognates of the first base type and a primed template nucleic acid of the array; (c) detecting the stabilized ternary complexes in the array; (d) repeating steps (b) and (c) for nucleotide cognates of a second base type, then repeating steps (b) and (c) for the nucleotide cognates of the third base type and then repeating steps (b) and (c) for nucleotide cognates of a fourth base type, whereby primed template nucleic acids of the array and polymerases of the plurality of polymerases are retained in the array; (e) identifying the type of nucleotide that is present in each of the stabilized ternary complexes detected in step (c); (f) adding a nucleotide to the primer of each of the primed template nucleic acids, whereby the array includes extended primed template nucleic acids; and (g) repeating steps (b) through (e) using the extended primed template instead of the primed template nucleic acids and using a plurality of second polymerases instead of the plurality of polymerases.

A method for sequencing primed template nucleic acids can include steps of (a) providing an array of primed template nucleic acids; (b) delivering a plurality of polymerases and a plurality of nucleotide cognates of a first base type to the array, thereby forming stabilized ternary complexes each including a polymerase of the plurality of polymerases, a nucleotide of the plurality of nucleotide cognates of the first base type and a primed template nucleic acid of the array; (c) detecting the stabilized ternary complexes in the array; (d) repeating steps (b) and (c) for nucleotide cognates of a second base type, whereby primed template nucleic acids of the array and polymerases of the plurality of polymerases are retained in the array; (e) identifying the type of nucleotide that is present in each of the stabilized ternary complexes detected in step (c); (f) adding a nucleotide to the primer of each of the primed template nucleic acids, whereby the array includes extended primed template nucleic acids; and (g) repeating steps (b) through (e) using the extended primed template instead of the primed template nucleic acids and using a plurality of second polymerases instead of the plurality of polymerases.

A deblocking process when included in a method set forth herein can facilitate sequencing of a primed template nucleic acid. The deblocking process can be used to convert a reversibly terminated primer into an extendable primer. Primer extension can then be used to move the site of ternary complex formation to a different location along the template nucleic acid. Repeated cycles of extension, examination and deblocking can be used to reveal the sequence of template nucleic acid. Each cycle reveals a subsequent base in the template nucleic acid. Exemplary reversible terminator moieties, methods for incorporating them into primers and methods for modifying the primers for further extension (often referred to as 'deblocking') are set forth in U.S. Pat. Nos. 7,427,673; 7,414,116; 7,544,794; 7,956,171; 8,034,923; 8,071,755; 8,808,989; or 9,399,798. Further examples are set forth in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

A sequencing method can include multiple repetitions of cycles, or steps within cycles, set forth herein. For example, a cycle that includes examination and primer extension steps can be repeated multiple times. Optionally, the cycle can further include steps of deblocking primers, or washing away unused reactants or spent products between various steps. Accordingly, a primed template nucleic acid can be subjected at least 2, 5, 10, 25, 50, 100, 150, 200 or more repeated cycles of a method set forth herein. Fewer cycles can be carried out when shorter read lengths are adequate. As such, a primed template nucleic acid can be subjected to at most 200, 150, 100, 50, 25, 10, 5 or 2 cycles of a method set forth herein.

In some embodiments, a sequencing method can be carried out for a predetermined number of repeated cycles. Alternatively, the cycles can be repeated until a particular empirically observed state is reached. For example, cycles can be repeated so long as signal is above an observable threshold, noise is below an observable threshold or signal-to-noise ratio is above an observable threshold.

Although embodiments of the present disclosure are exemplified herein with regard to sequencing reactions that employ repeated cycles, the cycles need not be repeated nor do the cycles need to include primer extension steps. For example, genotyping can be carried out by examining a single nucleotide position in a template nucleic acid via formation of a stabilized ternary complex. Genotyping can be carried out using serial delivery and/or accumulation of nucleotide cognates for different base types. Examples of genotyping techniques that can be modified to employ the nucleotide delivery methods set forth herein include those set forth in commonly owned U.S. Pat. No. 9,932,631 which is incorporated herein by reference.

Any of a variety of polymerases can be used in a method or apparatus set forth herein, for example, to form a stabilized ternary complex or to carry out primer extension. Polymerases that may be used include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that have the ability to catalyze a polymerization reaction. Optionally, the naturally occurring and/or modified variations thereof have the ability to catalyze a polymerization reaction in at least one condition that is not used during formation or examination of a stabilized ternary complex. Optionally, the naturally-occurring and/or modified variations that participate in stabilized ternary complexes have modified properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, reduced catalysis rates, catalytic inactivity etc. Mutant polymerases include, for example, polymerases wherein one or more amino acids are replaced with other amino acids, or insertions or deletions of one or more amino acids. Exemplary polymerase mutants that can be used to form a stabilized ternary complex include, for example, those set forth in U.S. patent application Ser. No. 15/866,353, published as US Pat. App. Pub. No. 2018/0155698 A1 or US Pat. App. Pub. No. 2017/0314072, each of which is incorporated herein by reference.

Modified polymerases include polymerases that contain an exogenous label moiety (e.g., an exogenous fluorophore), which can be used to detect the polymerase. Optionally, the label moiety can be attached after the polymerase has been at least partially purified using protein isolation techniques. For example, the exogenous label moiety can be covalently linked to the polymerase using a free sulfhydryl or a free amine moiety of the polymerase. This can involve covalent linkage to the polymerase through the side chain of a cysteine residue, or through the free amino group of the N-terminus. An exogenous label moiety can also be attached to a polymerase via protein fusion. Exemplary label moieties that can be attached via protein fusion include, for example, green fluorescent protein (GFP), phycobiliproteins (e.g. phycocyanin and phycoerythrin) or wavelength-shifted variants of GFP or phycobiliproteins. In some embodiments, an exogenous label on a polymerase can function as a member of a FRET pair. The other member of the FRET pair can be an exogenous label that is attached to a nucleotide that binds to the polymerase in a stabilized ternary complex. As such, the stabilized ternary complex can be detected or identified via FRET.

Alternatively, a polymerase that participates in a stabilized ternary complex, or that is used to extend a primer need not be attached to an exogenous label. For example, the polymerase need not be covalently attached to an exogenous label. Instead, the polymerase can lack any label until it associates with a labeled nucleotide and/or labeled nucleic acid (e.g. labeled primer and/or labeled template).

Different activities of polymerases can be exploited in a method set forth herein. A polymerase can be useful, for example, in a primer extension step, examination step or combination thereof. The different activities can follow from differences in the structure (e.g. via natural activities, mutations or chemical modifications). Nevertheless, polymerase can be obtained from a variety of known sources and applied in accordance with the teachings set forth herein and recognized activities of polymerases. Useful DNA polymerases include, but are not limited to, bacterial DNA polymerases, eukaryotic DNA polymerases, archaeal DNA polymerases, viral DNA polymerases and phage DNA polymerases. Bacterial DNA polymerases include E. coli DNA polymerases I, II and III, IV and V, the Klenow fragment of E. coli DNA polymerase, Clostridium stercorarium (Cst) DNA polymerase, Clostridium thermocellum (Cth) DNA polymerase and Sulfolobus solfataricus ($S_{So}$) DNA polymerase. Eukaryotic DNA polymerases include DNA polymerases $\alpha$, $\beta$, $\gamma$, $\delta$, $\epsilon$, $\eta$, $\zeta$, $\lambda$, $\sigma$, $\mu$, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cp7 DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus species* 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated herein by reference.

Useful RNA polymerases include, but are not limited to, viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V; and Archaea RNA polymerase.

Another useful type of polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some embodiments. Polymerases that substantially lack 3'-5' proofreading exonuclease activity are also useful in some embodiments, for example, in most genotyping and sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

A stabilized ternary complex, or a component that is capable of participating in the formation of a ternary complex, can be attached to a solid support. The solid support can be made from any of a variety of materials used for analytical biochemistry. Suitable materials may include glass, polymeric materials, silicon, quartz (fused silica), borofloat glass, silica, silica-based materials, carbon, metals, an optical fiber or bundle of optical fibers, sapphire, or plastic materials. The material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, ease of manipulation, or low cost of manufacture.

A particularly useful solid support is a particle such as a bead or microsphere. Populations of beads can be used for attachment of populations of stabilized ternary complexes or components capable of forming the complexes (e.g. polymerases, templates, primers or nucleotides). In some embodiments, it may be useful to use a configuration whereby each bead has a single type of stabilized ternary complex or a single type of component capable of forming the complex. For example, an individual bead can be attached to a single type of ternary complex, a single type of primed template nucleic acid, a single type of primer, a single type of template, a single type of polymerase or a single type of nucleotide. Alternatively, different types of components need not be separated on a bead-by-bead basis. As such, a single bead can bear multiple different types of ternary complexes, template nucleic acids, primers, primed template nucleic acids and/or nucleotides. The composition of a bead can vary, depending for example, on the format, chemistry and/or method of attachment to be used. Exemplary bead compositions include solid supports, and chemical functionalities imparted thereto, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

The geometry of a particle, such as a bead or microsphere, also can correspond to a wide variety of different forms and shapes. For example, a particle can be symmetrically shaped (e.g. spherical or cylindrical) or irregularly shaped (e.g. controlled pore glass). In addition, particles can be porous, thus increasing the surface area available for capture of ternary complexes or components thereof. Exemplary sizes for beads used herein can range from nanometers to millimeters or from about 10 nm-1 mm.

In particular embodiments, beads can be arrayed or otherwise spatially distinguished. Exemplary bead-based arrays that can be used include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

As will be recognized from the above bead array embodiments, a method of the present disclosure can be carried out in a multiplex format whereby multiple different types of nucleic acids are detected in parallel. Although it is also possible to serially process different types of nucleic acids using one or more steps of the methods set forth herein, parallel processing can provide cost savings, time savings and uniformity of conditions. An apparatus or method of the present disclosure can include at least 2, 10, 100, $1 \times 10^3$, $1 \times 10^4$, $1 \times 10^5$, $1 \times 10^6$, $1 \times 10^9$, or more different nucleic acids. Alternatively or additionally, an apparatus or method of the present disclosure can include at most $1 \times 10^9$, $1 \times 10^6$, $1 \times 10^5$, $1 \times 10^4$, $1 \times 10^3$, 100, 10, 2 or fewer, different nucleic acids. Accordingly, various reagents or products set forth herein as being useful in the apparatus or methods (e.g. primed template nucleic acids or stabilized ternary complexes) can be multiplexed to have different types or species in these ranges. The different nucleic acids that are present in an array can be located at different features of the array. Thus, signals acquired from a feature will be indicative of a particular nucleic acid sequence present at the feature.

Further examples of commercially available arrays that can be used include, for example, an Affymetrix GeneChip™ array. A spotted array can also be used according to some embodiments. An exemplary spotted array is a CodeLink™ Array commercialized by from Amersham Biosciences. Another array that is useful is one that is manufactured using inkjet printing methods such as SurePrint™ Technology commercialized by Agilent Technologies.

Other useful arrays include those that are used in nucleic acid sequencing applications. For example, arrays that are used to attach amplicons of genomic fragments (often referred to as clusters) can be particularly useful. Examples of nucleic acid sequencing arrays that can be used herein include those described in Bentley et al., *Nature* 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

A nucleic acid can be attached to a support in a way that provides detection at a single molecule level or at an ensemble level. For example, a plurality of different nucleic acids can be attached to a solid support in a way that an individual stabilized ternary complex that forms on one nucleic acid molecule on the support can be distinguished from all neighboring ternary complexes that form on the nucleic acid molecules of the support. As such, one or more different templates can be attached to a solid support in a format where each single molecule template is physically isolated and detected in a way that the single molecule is resolved from all other molecules on the solid support.

Alternatively, a method of the present disclosure can be carried out for one or more nucleic acid ensembles, an ensemble being a population of nucleic acids having a common template sequence. An ensemble can include, for example, at least 2, 10, 50, 100, 500, 1000 or more nucleic acids having a common template sequence. Alternatively or additionally, an ensemble can include at most 1000, 500, 100, 50, 10 or 2 nucleic acids having a common template sequence. An ensemble that is present at a feature of an array can be clonal such that substantially all of the nucleic acids at the feature have a common template sequence. However, a feature need not contain a clonal population of nucleic acids. Rather, a feature can include a mixed population of nucleic acids, wherein a particular template sequence is present in a majority of the nucleic acids. For example, a population of nucleic acids that are at a particular feature can include at least 51%, 60%, 75%, 90%, 95% or 99% or more species having a particular template sequence. A feature having a non-clonal population of nucleic acids can be detected under conditions that allow the population to be detected as an ensemble, whereby the total signal acquired from the feature represents an average of signals produced by the non-clonal population. So long as contaminating nucleic acids are present as a minority at a feature of interest, the average signal can provide a means to characterize the majority of template nucleic acids at the feature.

Cluster methods can be used to attach one or more ensembles to a solid support. As such, an array can have a plurality of ensembles, each of the ensembles being referred to as a cluster or array feature in that format. Clusters can be formed using methods known in the art such as bridge amplification or emulsion PCR. Useful bridge amplification methods are described, for example, in U.S. Pat. No. 5,641,658 or 7,115,400; or U.S. Patent Pub. Nos. 2002/0055100 A1; 2004/0002090 A1; 2004/0096853 A1; 2007/0128624 A1; or 2008/0009420 A1. Emulsion PCR methods include, for example, methods described in Dressman et al., *Proc. Natl. Acad. Sci. USA* 100:8817-8822 (2003), WO 05/010145, or U.S. Patent Pub. Nos. 2005/0130173 A1 or 2005/0064460 A1, each of which is incorporated herein by reference in its entirety. Another useful method for amplifying nucleic acids on a surface is rolling circle amplification (RCA), for example, as described in Lizardi et al., *Nat. Genet.* 19:225-232 (1998) or US 2007/0099208 A1, each of which is incorporated herein by reference.

In particular embodiments, a stabilized ternary complex, polymerase, primer, template, primed template nucleic acid or nucleotide is attached to a flow cell surface or to a solid support in a flow cell. A flow cell allows convenient fluidic manipulation by passing solutions into and out of a fluidic chamber that contacts the support-bound, ternary complex. The flow cell also provides for detection of the fluidically manipulated components. For example, a detector can be positioned to detect signals from the solid support, such as signals from a label that is recruited to the solid support due to formation of a stabilized ternary complex. Exemplary flow cells that can be used are described, for example, in US Pat. App. Pub. No. 2010/0111768 A1, WO 05/065814 or US Pat. App. Pub. No. 2012/0270305 A1, each of which is incorporated herein by reference.

Nucleic acids that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Thus, template nucleic acids used herein can be derived from a biological source, synthetic source or amplification product. Primers used herein can be DNA, RNA or analogs thereof.

Particularly useful nucleic acid templates are genome fragments that each include a sequence identical to a portion of a genome. A population of genome fragments can cover all or part of the sequence of a particular genome. For example, a population of genome fragments can include sequences for at least 5%, 10%, 20%, 30%, 40%, 50%, 60%, 70%, 75%, 80%, 85%, 90%, 95% or 99% of a genome. A genome fragment can have, for example, a sequence that is substantially identical to at least about 25, 50, 70, 100, 200, 300, 400, 500, 600, 700, 800, 900 or 1000 or more contiguous nucleotides of a genome. Alternatively or additionally, a genome fragment can have a sequence that is substantially identical to no more than $1\times10^5$, $1\times10^4$, $1\times10^3$, 800, 600, 400, 200, 100, 75, 50 or 25 contiguous nucleotides of a genome. A genome fragment can be DNA, RNA, or an analog thereof.

Exemplary organisms from which nucleic acids can be derived include, for example, a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Nucleic acids can also be derived from a prokaryote such as a bacterium, *Escherichia coli*, staphylococci or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. No. 6,355,431 or 9,045,796, each of which is incorporated herein by reference. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

Optionally, a plurality of primed template nucleic acids is attached to a solid support in an apparatus of the present disclosure. The solid support can include any of a variety of materials set forth herein including, for example, materials set forth herein in the context of nucleic acid arrays. The plurality of primed template nucleic acids can be attached to a feature of the array and, optionally, the templates that are attached to the feature can have the same sequence. Any of a variety of reagents set forth herein can be attached to a solid support instead of the primed template nucleic acids or, alternatively, in addition to attached primed template nucleic acids. In particular embodiments, an apparatus of the present disclosure need not be attached to reagents of any type.

In particular embodiments, an apparatus of the present disclosure includes a vessel, such as a manufactured vessel. The vessel can contain a plurality of primed template nucleic acids along with other reagents or reaction products that participate in a method set forth herein. A particularly useful manufactured vessel is a flow cell, examples of which are set forth herein above.

A system of the present disclosure can be configured for detecting nucleic acids, for example, using methods set forth herein. For example, a system can be configured to produce and detect ternary complexes formed between a polymerase and a primed template nucleic acid in the presence of nucleotides to identify one or more bases in a template nucleic acid sequence. Optionally, the system includes components and reagents for performing one or more steps set forth herein including, but not limited to, forming at least one stabilized ternary complex between a primed template nucleic acid, polymerase and next correct nucleotide; detecting the stabilized ternary complex(es); extending the primer of each primer-template hybrid; deblocking a reversibly terminated primer; and/or identifying a nucleotide, or sequence of nucleotides in the template.

A system of the present disclosure can include a vessel, solid support or other apparatus for carrying out a nucleic acid detection method. For example, the system can include an array, flow cell, multi-well plate, test tube, channel in a substrate, collection of droplets or vesicles, tray, centrifuge tube, tubing or other convenient apparatus. The apparatus can be removable, thereby allowing it to be placed into or removed from the system. As such, a system can be configured to process a plurality of apparatus (e.g. vessels or solid supports) sequentially or in parallel. The system can include a fluidic component having reservoirs for containing one or more of the reagents set forth herein (e.g. polymerase, primer, template nucleic acid, nucleotide(s) for ternary complex formation, nucleotides for primer extension, deblocking reagents, ternary complex inhibitors, or mixtures of such components). The fluidic system can be configured to deliver reagents to a vessel or solid support, for example, via channels or droplet transfer apparatus (e.g. electrowetting apparatus). Any of a variety of detection apparatus can be configured to detect the vessel or solid support where reagents interact. Examples include luminescence detectors, surface plasmon resonance detectors and others known in the art. Exemplary systems having fluidic and detection components that can be readily modified for use in a system herein include, but are not limited to, those set forth in US Pat. App. Pub. No. 2018/0280975A1, which claims priority to U.S. Pat. App. Ser. No. 62/481,289; U.S. Pat. Nos. 8,241,573; 7,329,860 or 8,039,817; or US Pat. App. Pub. Nos. 2009/0272914 A1 or 2012/0270305 A1, each of which is incorporated herein by reference.

Optionally, a system of the present disclosure further includes a computer processing unit (CPU) that is configured to operate system components. The same or different CPU can interact with the system to acquire, store and process signals (e.g. signals detected in a method set forth herein). In particular embodiments, a CPU can be used to determine, from the signals, the identity of the nucleotide that is present at a particular location in a template nucleic acid. In some cases, the CPU will identify a sequence of nucleotides for the template from the signals that are detected.

A useful CPU can include one or more of a personal computer system, server computer system, thin client, thick client, hand-held or laptop device, multiprocessor system, microprocessor-based system, set top box, programmable consumer electronic, network PC, minicomputer system, mainframe computer system, smart phone, and distributed cloud computing environments that include any of the above systems or devices, and the like. The CPU can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The CPU may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to carry out one or more steps of a method set forth herein. For example, executable instructions may include an operating system, one or more application programs, other program modules, and program data. Generally, program modules may include routines, programs, objects, components, logic, data structures, and so on, that perform particular tasks set forth herein.

The components of a CPU may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A CPU can optionally communicate with one or more external devices such as a keyboard, a pointing device (e.g. a mouse), a display, such as a graphical user interface (GUI), or other device that facilitates interaction with the nucleic acid detection system. Similarly, the CPU can communicate with other devices (e.g., via network card, Bluetooth™, WiFi, modem, etc.). Such communication can occur via I/O interfaces. Still yet, a CPU of a system herein may communicate with one or more networks such as a local area network (LAN), a general wide area network (WAN), and/or a public network (e.g., the Internet) via a suitable network adapter.

EXAMPLE I

Efficient Methods for Delivering Nucleotides in a Sequencing By Binding™ Procedure This example describes Sequencing By Binding™ procedures in which different types of nucleotides are delivered serially to an array of template nucleic acids, in the presence of a polymerase, to form ternary complexes. Examination steps are carried out after each delivery to distinguish one type of ternary complex from another. The results presented here demonstrate that altering reagent delivery or wash steps led to improvements such as decreased cycle time, decreased reagent consumption and improved sequencing results.

Flow cells containing primed template nucleic acids were prepared as follows. Template nucleic acid strands synthesized in 12 PCR reactions using 5'-biotinylated primers were prepared, and then independently bound to streptavidin-coated magnetic beads. This resulted in a population of 12 bead types, where each bead harbored a homogenous collection of template strands. Beads used in the procedure had been functionalized with 1 mM NHS-PEG4-TCO in phosphate buffered saline (PBS). Beads harboring immobilized template strands were next flowed over an aminosilane flow cell surface that had been functionalized with tetrazine. The mixture was incubated for one hour to permit covalent attachment of the decorated beads to the functionalized surface within the flow cell. Next, sequencing primers were flowed into the flow cell and allowed to hybridize to the immobilized template strands.

Sequencing was performed by repeated cycles. The sequencing cycle was initiated by incorporating reversible terminator nucleotides at the 3'-ends of the hybridized sequencing primers to create a collection of blocked primed template nucleic acid molecules. This was accomplished by delivery of RTS solution to the flow cell (RTS contained: 50 mM Tricine pH 8.4, 0.1% Tween-80, 40 U/ml Therminator™ polymerase, 5 mM $MgCl_2$, 0.1% hydroxylamine, 50 mM KCl, 0.1% Tween-80, 0.1 mM EDTA, and 200 nM of unlabeled reversibly terminated nucleotide analogs of dATP, dGTP, dCTP, and dTTP). The reversible terminator nucleotide used in this illustrative procedure included a 3'-$ONH_2$ reversible terminator moiety. A description of this reversible terminator nucleotide can be found in U.S. Pat. No. 7,544,794, the disclosure of which is incorporated herein by reference. The flow cell was then washed with ESB solution (1 M guanidinium thiocyanate, 60 mM HEPES, 0.1% Tween-80, 0.1% hydroxylamine and 2 mM EDTA) followed by a wash with PRE solution (50 mM Tricine pH 8.4, 50 mM KCl, 0.1% Tween-80, 0.1% hydroxylamine and 0.1 mM EDTA).

The cycle then continued with an examination subroutine in which four different nucleotides were sequentially delivered to the flow cell. Reversible terminator moieties on the 3' nucleotides of the primer strands precluded nucleotide incorporation during the ternary complex formation and detection steps. In standard conditions, one of the four different labeled nucleotides was delivered to the flow cell in EXAM solution (Cy5-dNTP (400 nM for each of Cy5-dATP, Cy5-dGTP or Cy5-dCTP; or 800 nM for Cy5-dTTP), 1 mM $MgCl_2$, and 20 U/ml Therminator™ polymerase in IMG solution), followed by a wash with IMG solution (20 mM Tricine pH 7.0, 1M betaine, 50 mM LiCl, 0.1% Tween-80, 50 mM KCl, 10 mM ammonium Sulfate, 0.1% hydroxylamine, and 0.1 mM EDTA). The Cy5-dNTP nucleotides are described in U.S. patent application Ser. No. 15/873,343, published as US Pat. App. Pub. No. 2018/0208983 A1, which is incorporated herein by reference. The flow cell was imaged via fluorescence microscopy to detect ternary complexes that were retained in the IMG solution. Following imaging the flow cell was washed with ESB solution and then with PRE solution. The steps of the subroutine were repeated for each of the four nucleotide types individually. The examination subroutine was modified in several experiments as set forth below in the context of the figures.

Following the examination subroutine, the sequencing cycle continued with removal of the reversible terminator moiety from the primers by treating the flow cell the solution containing 0.25 M sodium acetate and 0.7 M sodium nitrite titrated to pH 4.8 with acetic acid. The flow cell was then washed in PRE solution to remove the sodium acetate and sodium nitrite. The sequencing process then returned to the sequencing cycle initiation step.

FIG. 1 shows a plot of signal intensity vs. sequencing cycle for the Sequencing By Binding™ protocol that used the standard conditions as set forth above. Individual traces are shown for the 'on' intensity detected for each nucleotide type and for the 'off' intensity for each nucleotide type. For each bead in each cycle, the nucleotide type that produced the highest signal was identified as the 'on' signal and the other three nucleotide types were identified as the 'off' signal. The 'on' signals for each nucleotide type were averaged across all bead types detected in a given cycle, and the average intensity was plotted across 100 cycles to obtain each of the 'on' signal traces shown in the figure. Similar averaging of signal intensities across all bead types on a per cycle basis was used to arrive at the 'off' intensity traces shown in FIG. 1.

Signal decay for the 'on' traces was evaluated by fitting the traces to a curve defined by the following formula:

$$I=I_0 e^{-(n/\tau)} \quad \text{(Formula 1)}$$

wherein I is signal intensity, n is the number of cycles and $\tau$ is the cycle when the signal is about 37% of $I_0$ (initial signal intensity). Higher $\tau$ is indicative of slower rate of signal decay, which is generally preferred for increased read length and sequencing accuracy, whereas faster rate of signal decay is characterized by lower values for $\tau$. The goodness of fit was calculated as the coefficient of determination, $R^2$. Higher $R^2$ values correlate with reduced signal intensity variance from variability in sequence context, whereas an increase in adverse impact of sequence context results in a lower $R^2$ value. The standard protocol traces shown in FIG. 1 had an average $\tau$ of 37 and an average $R^2$ of 0.88 (the averages were taken across the on traces for all four nucleotide types).

Experiments were run to test the effect of varying concentrations of NaCl in washes carried out between imaging steps in the examination routine. Specifically, ESB was replaced with salt solutions between imaging steps of the examination subroutine. The salt concentrations tested were 1 M GdSCN (standard wash), no salt, 64 mM NaCl, 160 mM NaCl, 400 mM NaCl, 1 M NaCl, and 2.5 M NaCl. The results indicated that 'on' signal intensities were higher when lower salt washes were used (e.g. 0, 64 or 160 mM salt) compared to when higher salt washes were used (400 mM NaCl, 1 M NaCl, 2.5 M NaCl and 1M GdSCN). The lower salt washes also resulted in less variation in signal intensities compared to standard washes.

Figure 2:
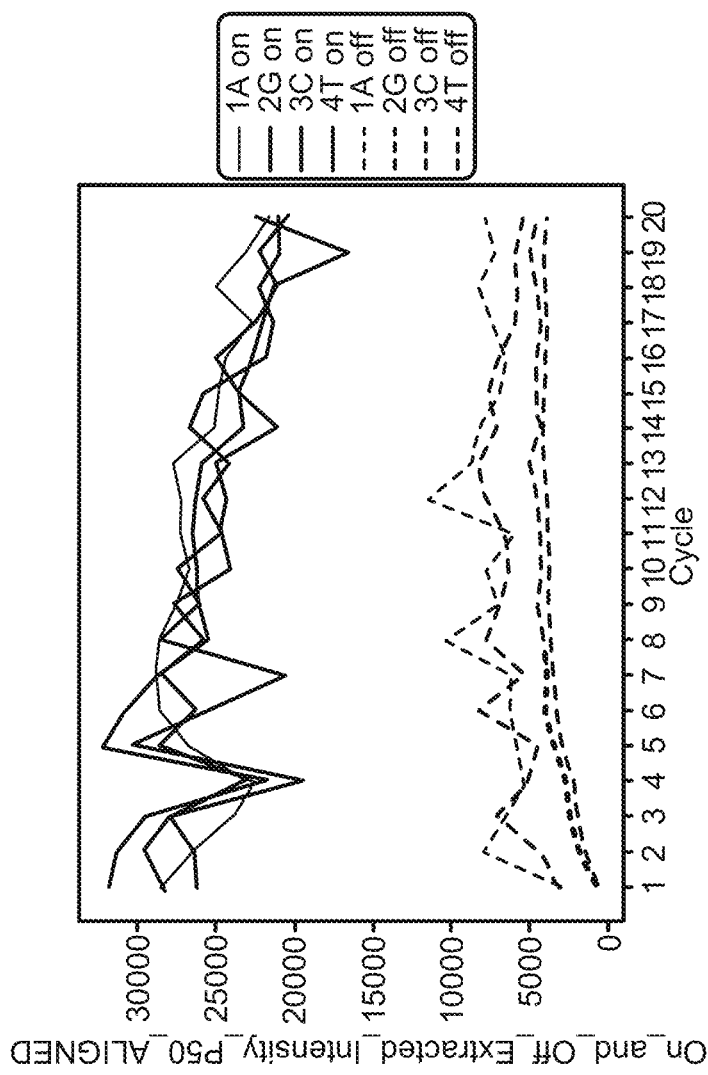
FIG. 2 shows a plot of 'on' and 'off' signal intensity vs. sequencing cycle for a sequencing protocol that includes steps of washing primed template nucleic acids to replace nucleotides between examination steps within a sequencing cycle, wherein polymerase was added prior to the first examination step.

FIG. 2 shows a plot of signal intensity vs. sequencing cycle for a Sequencing By Binding™ protocol in which polymerase was not included in the EXAM solutions that were delivered in the examination subroutine. Rather, polymerase was retained in the flow cell from the previous RTS delivery. The results indicated that, surprisingly, polymerase was retained across multiple reagent delivery and imaging steps carried out in the sequencing cycle. Moreover, retaining polymerase resulted in less variation in signal intensities compared to the standard procedure. However, 'off' intensities were higher, especially for C and T traces, when polymerase was retained compared to standard conditions.

Figure 3:
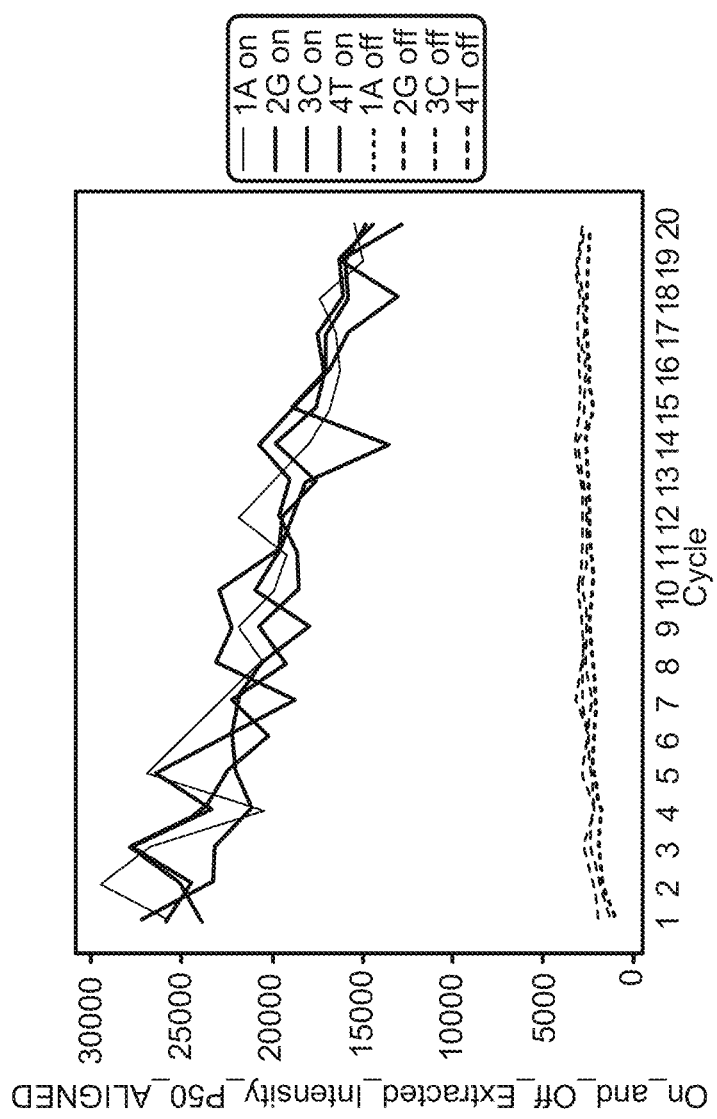
FIG. 3 shows a plot of 'on' and 'off' signal intensity vs. sequencing cycle for a sequencing protocol that includes steps of washing primed template nucleic acids with salt and ethanol between examination steps within a sequencing cycle, wherein polymerase was added prior to the first examination step.

FIG. 3 shows a plot of signal intensity vs. sequencing cycle for a Sequencing By Binding™ protocol in which the standard conditions were adjusted by replacing the ESB and PRE washes with a strip solution containing salt and ethanol. Specifically, the strip solution included 50 mM Tricine pH 8.4, 150 mM KCl, 0.1% Tween-80, 0.1% hydroxylamine and 0.1 mM EDTA and 25% ethanol. Also, in the modified conditions, polymerase was not included in any of the EXAM solutions that were delivered in the examination subroutine. Rather, polymerase was retained in the flow cell from the previous RTS delivery. As before, the results indicated that polymerase was retained across multiple reagent delivery and imaging steps carried out in the examination subroutine, and also indicated that retaining polymerase resulted in less variation in signal intensities compared to the standard procedure. However, use of ethanol along with high salt resulted in reduced 'off' intensities, an improvement compared to the results of FIG. 2.

A sequencing protocol was performed for 150 cycles under the conditions described for FIG. 3. The value of $\tau=53$ for the run indicated an improvement in signal decay compared to $\tau=37$ for the standard conditions plotted in FIG. 1. The use of salt/ethanol washes in the examination subroutine also resulted in reduced sequence context artifacts for the modified run ($R^2=0.94$) compared to the standard conditions of FIG. 1 ($R^2=0.88$).

A sequencing protocol was performed for 100 cycles in which the standard conditions were adjusted by omitting the ESB and PRE washes between imaging steps. Also, in the modified conditions, polymerase was not included in any of the EXAM solutions that were delivered in the examination subroutine. Rather, polymerase was retained in the flow cell from the previous RTS delivery. Accordingly, ternary complexes of different types (i.e. ternary complexes having different types of cognate nucleotides bound thereto) accumulated during the examination subroutine. Under this condition, 'on' intensities were identified as the beads that showed the largest increase in signal intensity from one image to the next, albeit within a particular cycle. Signal decay was faster in the modified conditions ($\tau=27$) compared to standard conditions of FIG. 1 ($\tau=37$). However, the $R^2$ value of 0.97 for the modified condition was an improvement compared to the conditions of FIG. 1 ($R^2=0.88$), indicating that sequence context artifacts were reduced when ternary complexes accumulated over the examination subroutine. These results indicate that accumulation of ternary complexes provided very good sequencing results.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:
1. A method for identifying a nucleotide in a primed template nucleic acid, comprising
(a) providing an array of primed template nucleic acids;
(b) delivering a plurality of labeled nucleotide cognates of a first base type and a plurality of polymerases to the array, thereby forming stabilized ternary complexes each comprising a polymerase of the plurality of polymerases, a nucleotide of the plurality of labeled nucleotide cognates of the first base type and a primed template nucleic acid in the array;
(c) detecting the stabilized ternary complexes in the array that comprise the nucleotide cognates of the first base type;

(d) removing the plurality of labeled nucleotide cognates of the first base type from the ternary complex, whereby the primed template nucleic acids and the polymerases are retained in the array;

(e) delivering a plurality of labeled nucleotide cognates of a second base type to the array in the presence of polymerases from step (b), thereby forming stabilized ternary complexes each comprising a polymerase of the polymerases from step (b), a nucleotide of the plurality of nucleotide cognates of the second base type and a primed template nucleic acid in the array;

(f) detecting the stabilized ternary complexes in the array that comprise the nucleotide cognates of the second base type; and (g) identifying the type of labeled nucleotide that is present in each of the stabilized ternary complexes detected in step (c) and step (e).

2. The method of claim 1, further comprising repeating steps (e) and (f) using nucleotide cognates of a third base type instead of the nucleotide cognates of the second base type.

3. The method of claim 2, further comprising repeating steps (e) and (f) using nucleotide cognates of a fourth base type instead of the nucleotide cognates of the second base type.

4. The method of claim 1, wherein the nucleotide cognate of the first base type is removed by washing the array with an aqueous solution comprising at least 10% to at most 50% ethanol.

5. The method of claim 1, wherein the labels of the nucleotide cognates of the first base type produce different signals from the signals produced by the labels of the nucleotide cognates of the second base type.

6. The method of claim 5, wherein step (f) further comprises distinguishing the different signals from the different labels.

7. The method of claim 1, wherein the label on the nucleotide cognates of the first base type produce signals that are the same as the signals produced from the label on the nucleotide cognate of the second base type.

8. The method of claim 1, further comprising
(h) adding a nucleotide to the primer of each of the primed template nucleic acids, whereby the array comprises extended primed template nucleic acids;
(i) repeating steps (b) through (g) using the extended primed templates instead of the primed template nucleic acids.

9. The method of claim 1, wherein a second polymerase adds the nucleotide to the primer of each of the primed template nucleic acids and wherein the polymerase and the second polymerase are the same type of polymerase.

10. The method of claim 8, wherein the primer comprises a reversible terminator moiety and wherein step (h) comprises deblocking the primer and adding the nucleotide to the deblocked primer of each of the primed template nucleic acids, whereby the array comprises extended primed template nucleic acids.

11. A method for identifying a nucleotide in a primed template nucleic acid, comprising
(a) providing a vessel comprising a primed template nucleic acid, polymerase and a labeled nucleotide cognate of a first base type;
(b) examining the vessel for a stabilized ternary complex comprising the polymerase and the labeled nucleotide cognate of the first base type bound at a base position of the primed template nucleic acid;
(c) removing the labeled nucleotide cognates of the first base type from the ternary complex in the vessel;
(d) delivering a labeled nucleotide cognate of a second base type to the vessel, whereby the vessel retains the primed template nucleic acid and the polymerase from step (b);
(e) examining the vessel for a stabilized ternary complex comprising the polymerase and the labeled nucleotide cognate of the second base type bound at the base position of the primed template nucleic acid; and
(d) identifying the type of nucleotide at the base position of the primed template nucleic acid.

12. A method for identifying a nucleotide in a primed template nucleic acid, comprising
(a) providing an array of primed template nucleic acids;
(b) forming stabilized ternary complexes each comprising a polymerase, a labeled nucleotide cognate of a first base type and a primed template nucleic acid in the array;
(c) detecting the stabilized ternary complexes in the array;
(d) removing the plurality of labeled nucleotide cognates of the first base type from the ternary complex;
(e) repeating steps (b) and (c) for a labeled nucleotide cognate of a second base type, whereby the primed template nucleic acids and the polymerases are retained in the array; and
(f) identifying the type of nucleotide that is present in each of the stabilized ternary complexes detected in step (c).

13. A method for identifying a nucleotide in a primed template nucleic acid, comprising
(a) providing an array of primed template nucleic acids;
(b) delivering a plurality of polymerases and a plurality of labeled nucleotide cognates of a first base type to the array, thereby forming stabilized ternary complexes each comprising a polymerase of the plurality of polymerases, a labeled nucleotide of the plurality of labeled nucleotide cognates of the first base type and a primed template nucleic acid of the array;
(c) detecting the stabilized ternary complexes in the array;
(d) removing the plurality of labeled nucleotide cognates of the first base type from the ternary complex;
(e) repeating steps (b) and (c) for labeled nucleotide cognates of a second base type, whereby primed template nucleic acids of the array and polymerases of the plurality of polymerases are retained in the array; and
(f) identifying the type of nucleotide that is present in each of the stabilized ternary complexes detected in step (c).

* * * * *